United States Patent
Shimamura et al.

(10) Patent No.: US 9,901,317 B2
(45) Date of Patent: Feb. 27, 2018

(54) IMAGE PROCESSING APPARATUS FOR ACQUIRING A DYNAMIC IMAGE AND STORAGE MEDIUM

(71) Applicant: Konica Minolta, Inc., Tokyo (JP)

(72) Inventors: Kenta Shimamura, Takatsuki (JP); Hiroshi Yamato, Amagasaki (JP); Osamu Toyama, Kakogawa (JP); Shintaro Muraoka, Hachioji (JP); Sho Noji, Tachikawa (JP)

(73) Assignee: KONICA MINOLTA, INC., Tokyo (JP)

( * ) Notice: Subject to any disclaimer, the term of this patent is extended or adjusted under 35 U.S.C. 154(b) by 103 days.

(21) Appl. No.: 14/894,242

(22) PCT Filed: May 2, 2014

(86) PCT No.: PCT/JP2014/062130
§ 371 (c)(1),
(2) Date: Nov. 25, 2015

(87) PCT Pub. No.: WO2014/192504
PCT Pub. Date: Dec. 4, 2014

(65) Prior Publication Data
US 2016/0120491 A1 May 5, 2016

(30) Foreign Application Priority Data
May 31, 2013 (JP) .................................. 2013-115889

(51) Int. Cl.
*H04N 5/232* (2006.01)
*A61B 6/00* (2006.01)
(Continued)

(52) U.S. Cl.
CPC .............. *A61B 6/463* (2013.01); *A61B 6/486* (2013.01); *A61B 6/503* (2013.01); *G06K 9/6212* (2013.01);
(Continued)

(58) Field of Classification Search
CPC ....................................................... A61B 6/463
(Continued)

(56) References Cited

U.S. PATENT DOCUMENTS

2012/0300904 A1* 11/2012 Shimada .............. A61B 6/4291
378/62

FOREIGN PATENT DOCUMENTS

CN   102793551 A   11/2012
JP   S6462778 A    3/1989
(Continued)

OTHER PUBLICATIONS

Written Opinion of the International Searching Authority dated Aug. 19, 2014 for PCT/JP2014/062130 and English translation.
(Continued)

*Primary Examiner* — Joel Fosselman
(74) *Attorney, Agent, or Firm* — Lucas & Mercanti, LLP

(57) ABSTRACT

An image processing apparatus of the present invention includes: a dynamic image acquiring unit acquiring a dynamic image; a time range setting unit setting a first time range and a second time range in an overall time of the dynamic image; a thumbnail generating unit generating a first thumbnail image and a second thumbnail image that are still images obtained by performing statistical processing on frame images in the first time range and frame images in the second time range, respectively; and a display unit displaying the first thumbnail image and the second thumbnail image so that they can visually be compared with each other.

20 Claims, 25 Drawing Sheets

(51) Int. Cl.
  *G06K 9/62* (2006.01)
  *H04N 5/262* (2006.01)
  *H04N 5/32* (2006.01)
  *G06T 7/00* (2017.01)
  *G06T 7/12* (2017.01)
  *G06T 7/62* (2017.01)

(52) U.S. Cl.
  CPC .............. *G06T 7/0016* (2013.01); *G06T 7/12* (2017.01); *G06T 7/62* (2017.01); *H04N 5/232* (2013.01); *H04N 5/2621* (2013.01); *H04N 5/32* (2013.01); *A61B 6/502* (2013.01); *G06T 2207/10016* (2013.01); *G06T 2207/10116* (2013.01); *G06T 2207/30048* (2013.01); *G06T 2207/30104* (2013.01)

(58) Field of Classification Search
  USPC ..................................................... 348/333.05
  See application file for complete search history.

(56) References Cited

FOREIGN PATENT DOCUMENTS

| | | |
|---|---|---|
| JP | H0584237 A | 4/1993 |
| JP | 2005305113 A | 11/2005 |
| JP | 2008188165 A | 8/2008 |
| JP | 2009273671 A | 11/2009 |
| JP | 2012005729 A | 1/2012 |
| JP | 2012011120 A | 1/2012 |
| JP | 2012110399 A | 6/2012 |
| JP | 2012147949 A | 8/2012 |
| WO | 2006137294 A1 | 12/2006 |

OTHER PUBLICATIONS

International Search Report dated Aug. 19, 2014 for PCT/JP2014/062130 and English translation.
Office Action dated Sep. 22, 2017 from the corresponding Chinese Application No. CN 201480030241.9 and English translation.

* cited by examiner

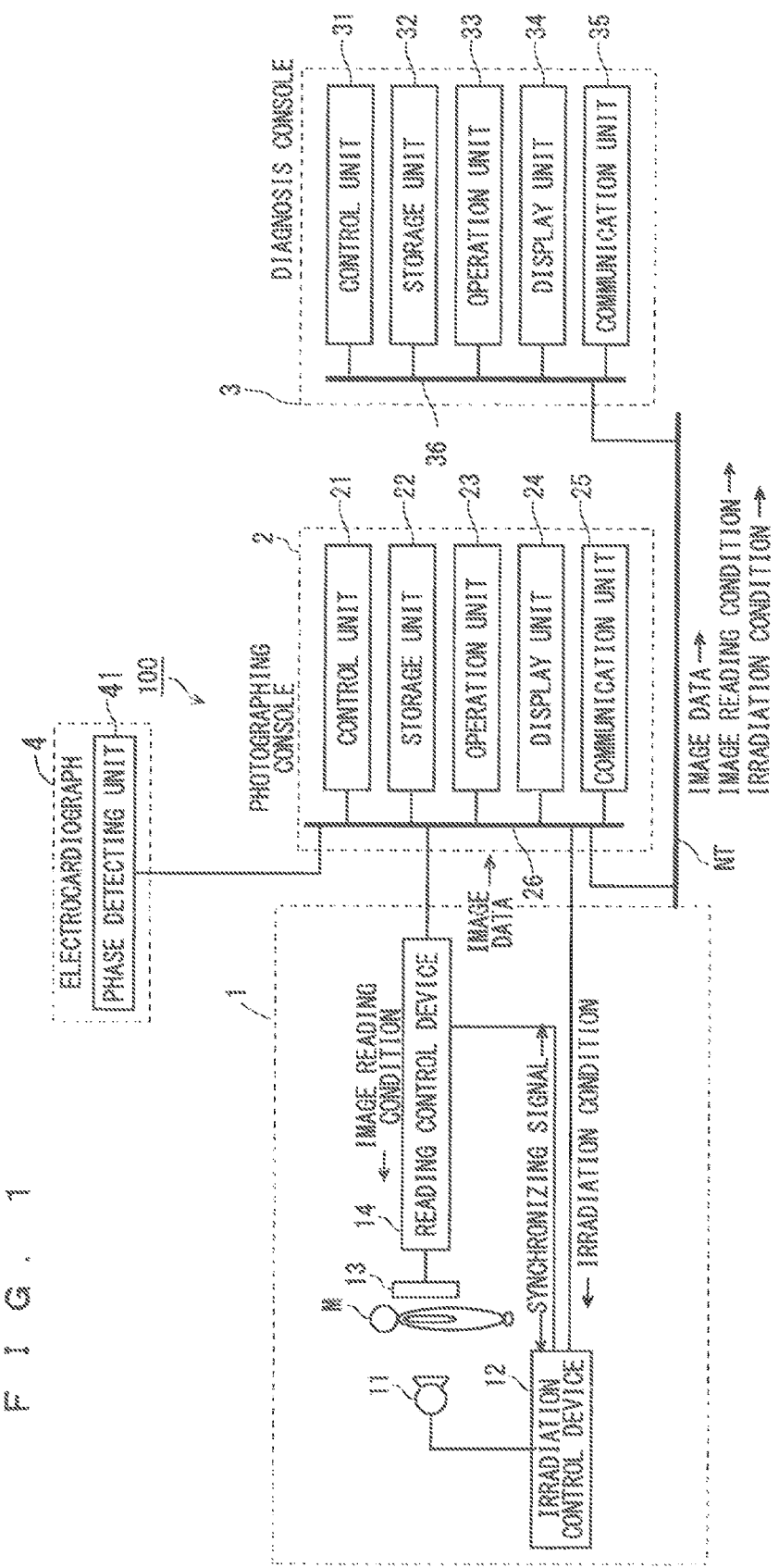

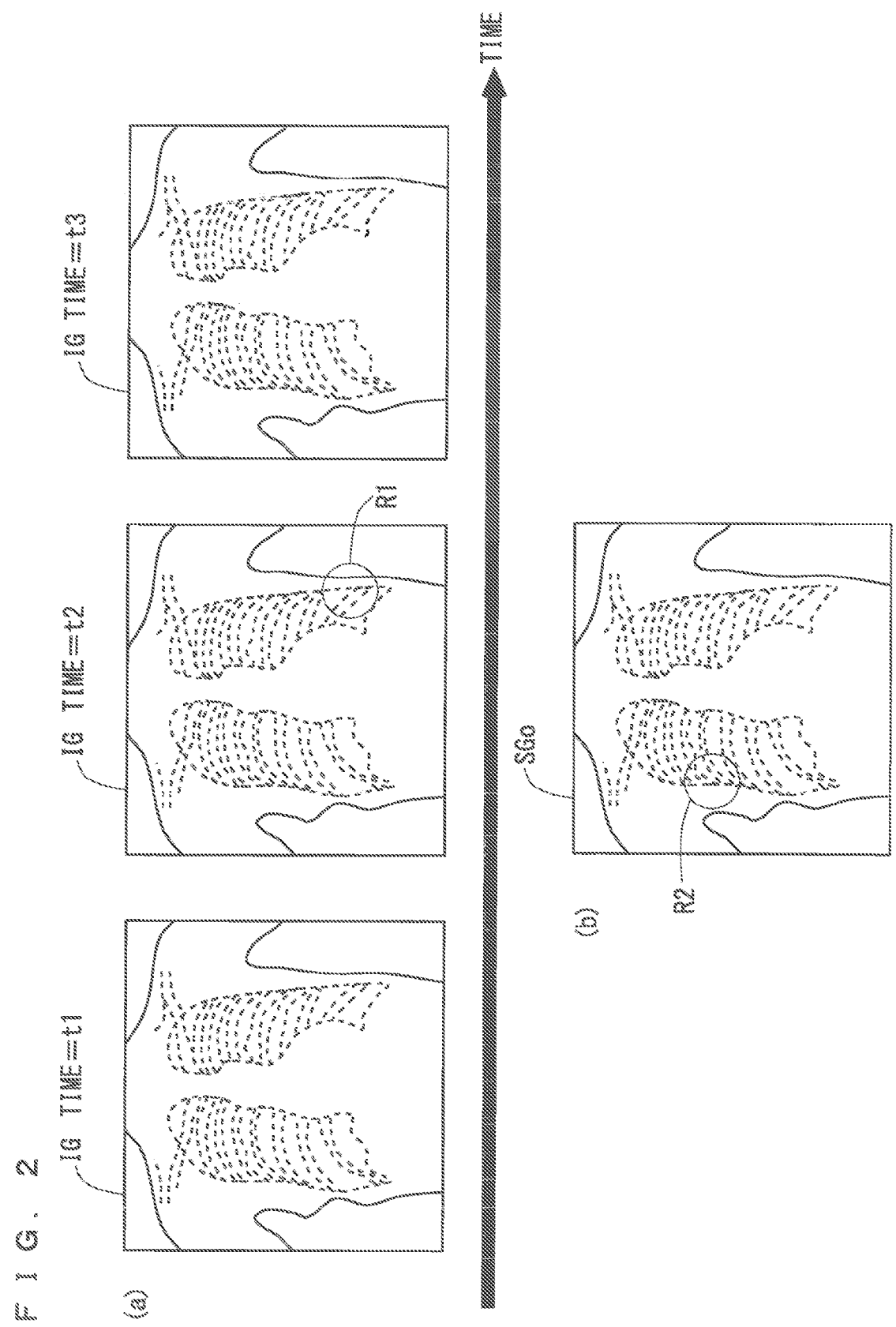

F I G . 5
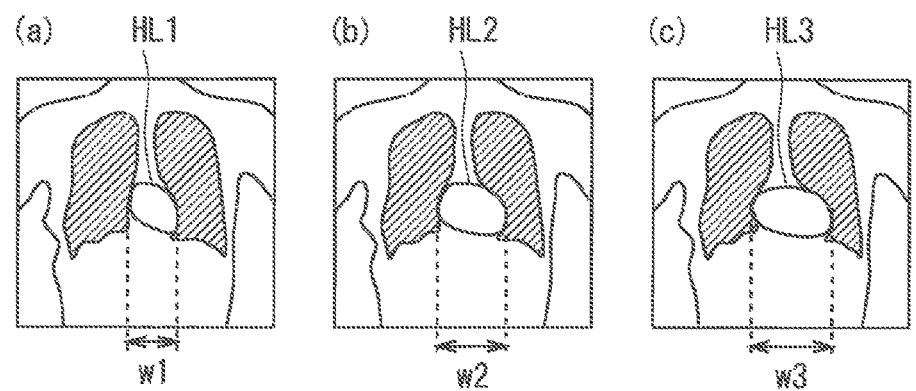

F I G. 7
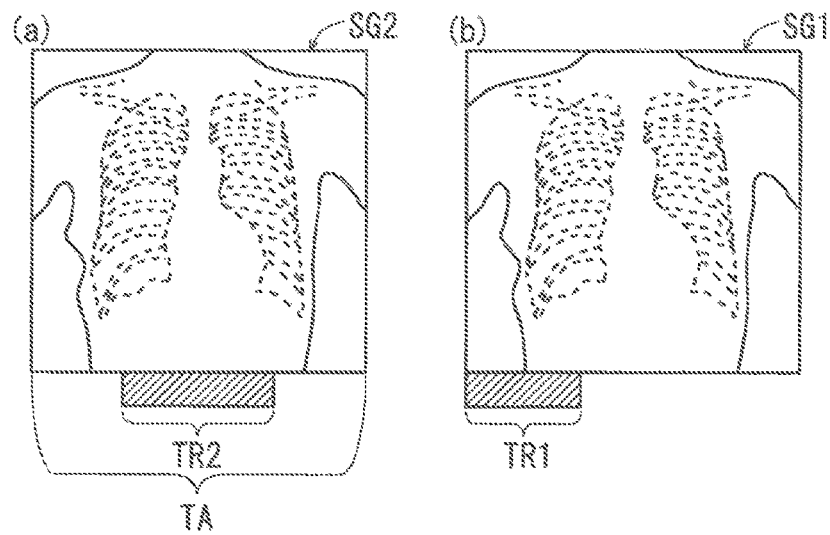
F I G. 8
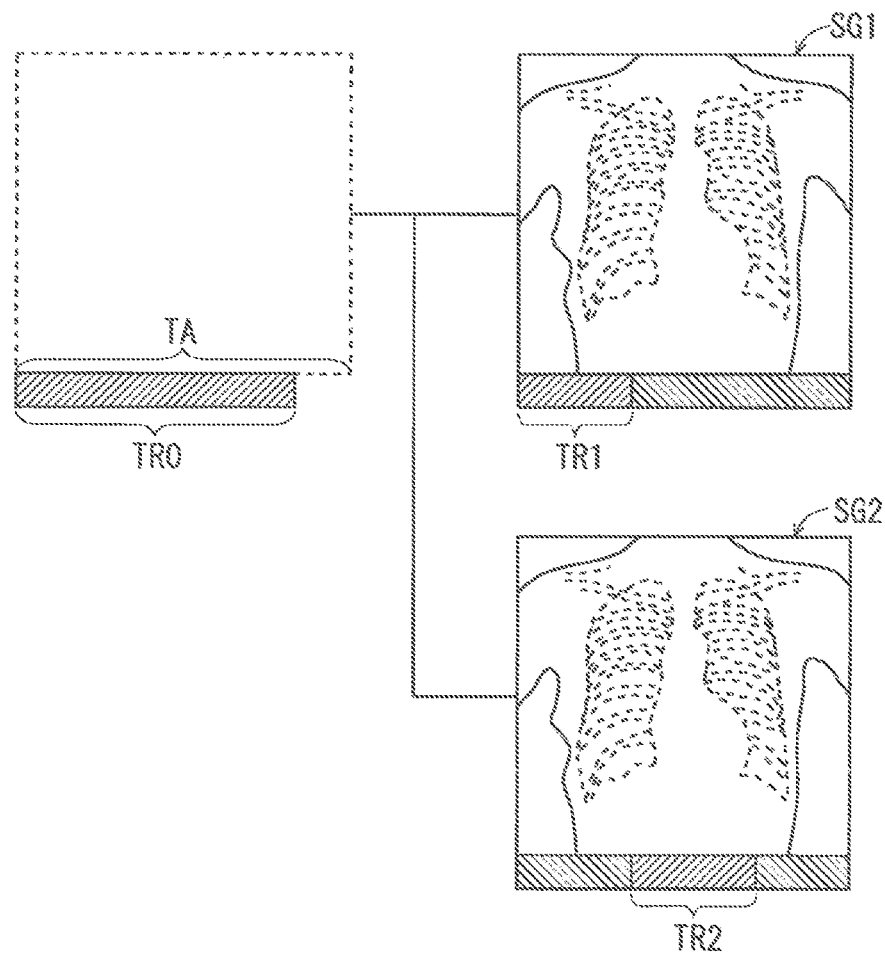

F I G. 1 4
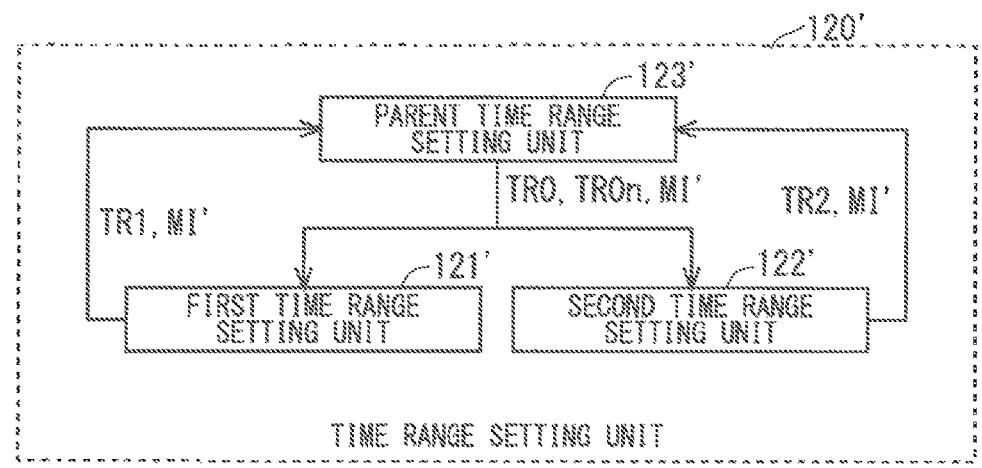

FIG. 16
(a)
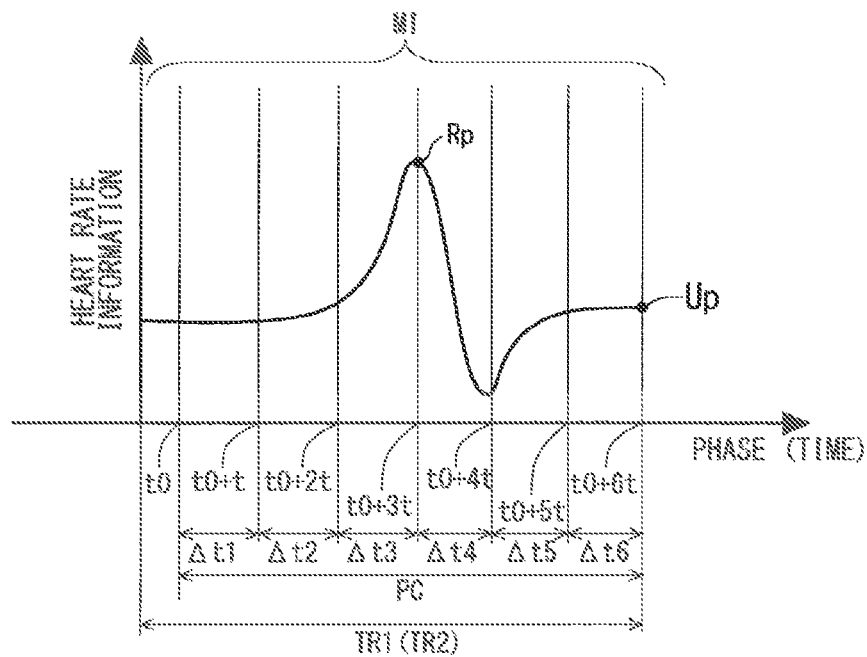
(b)
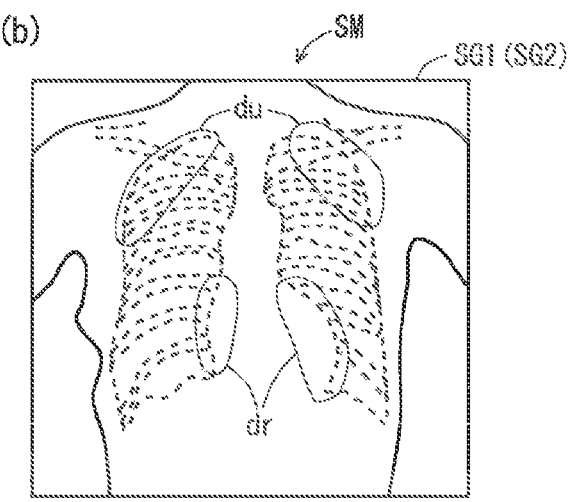

F I G. 1 9
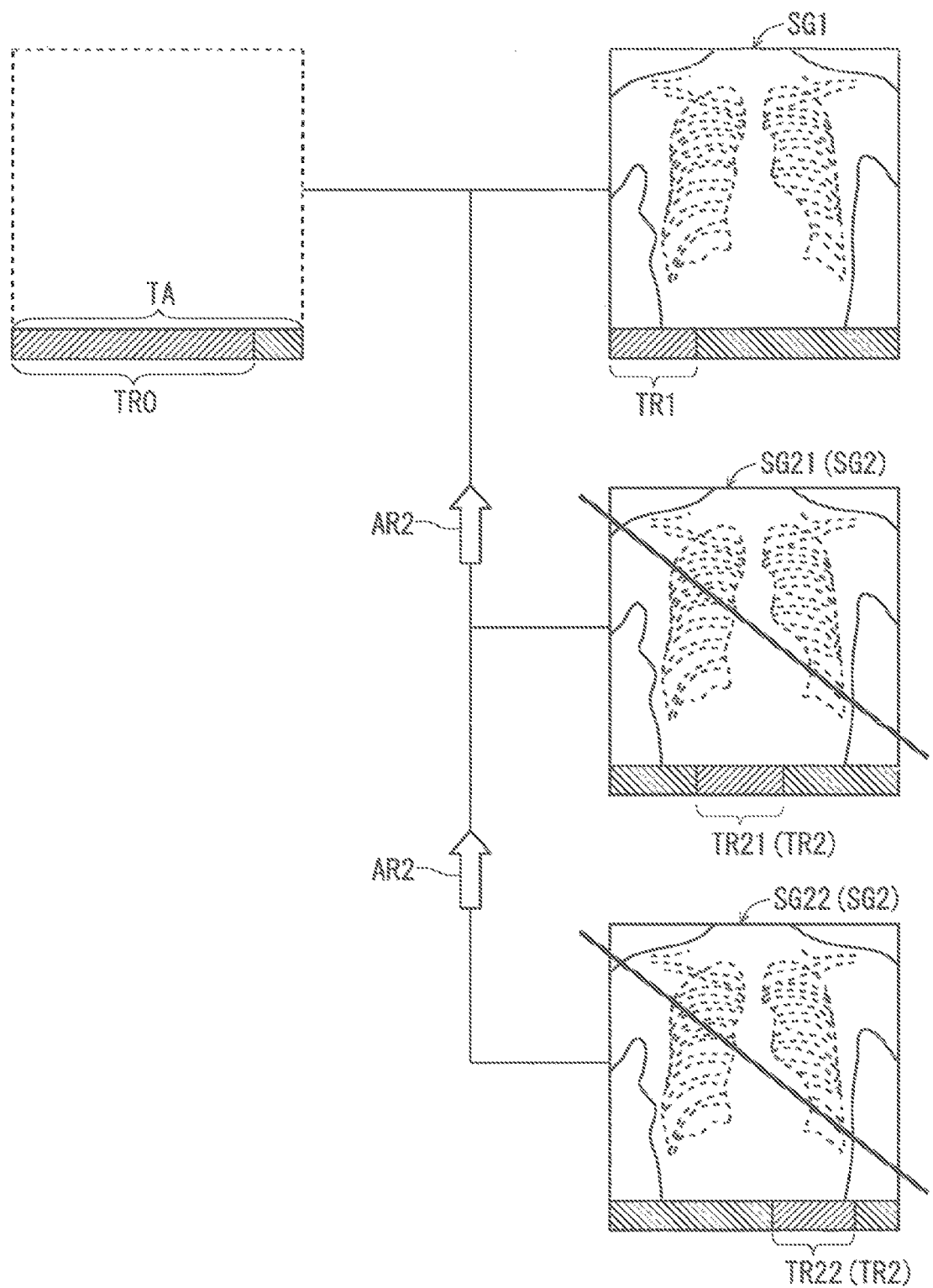

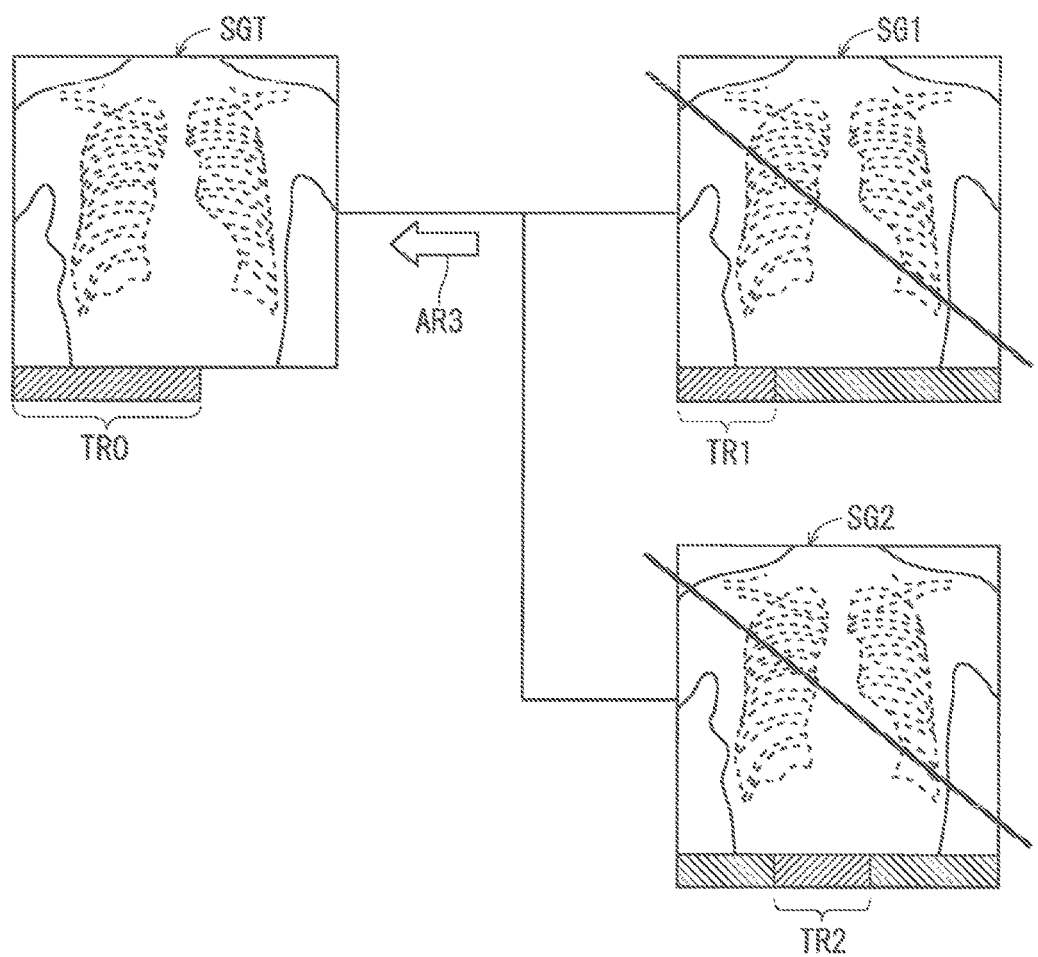

F I G. 2 3
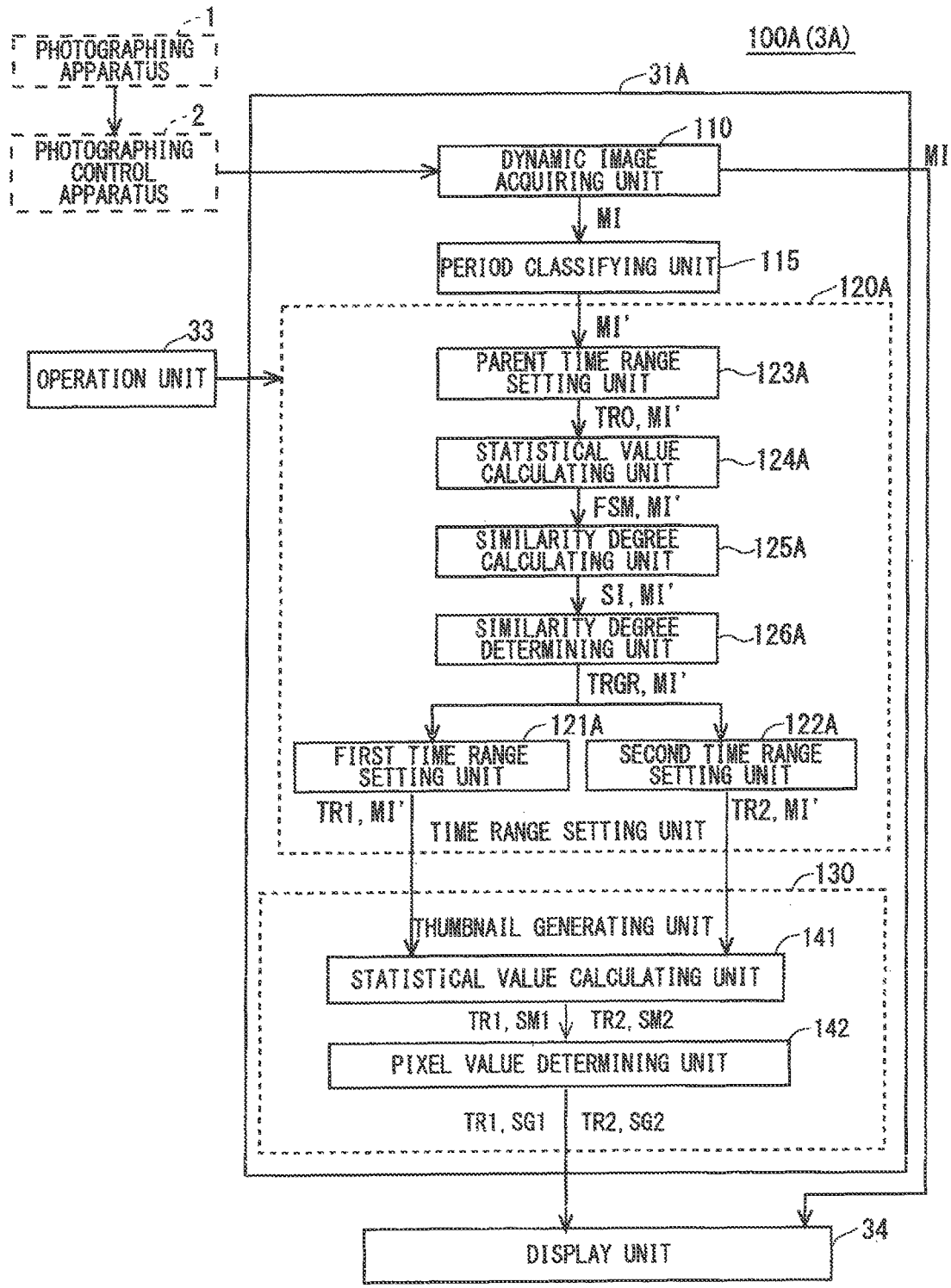

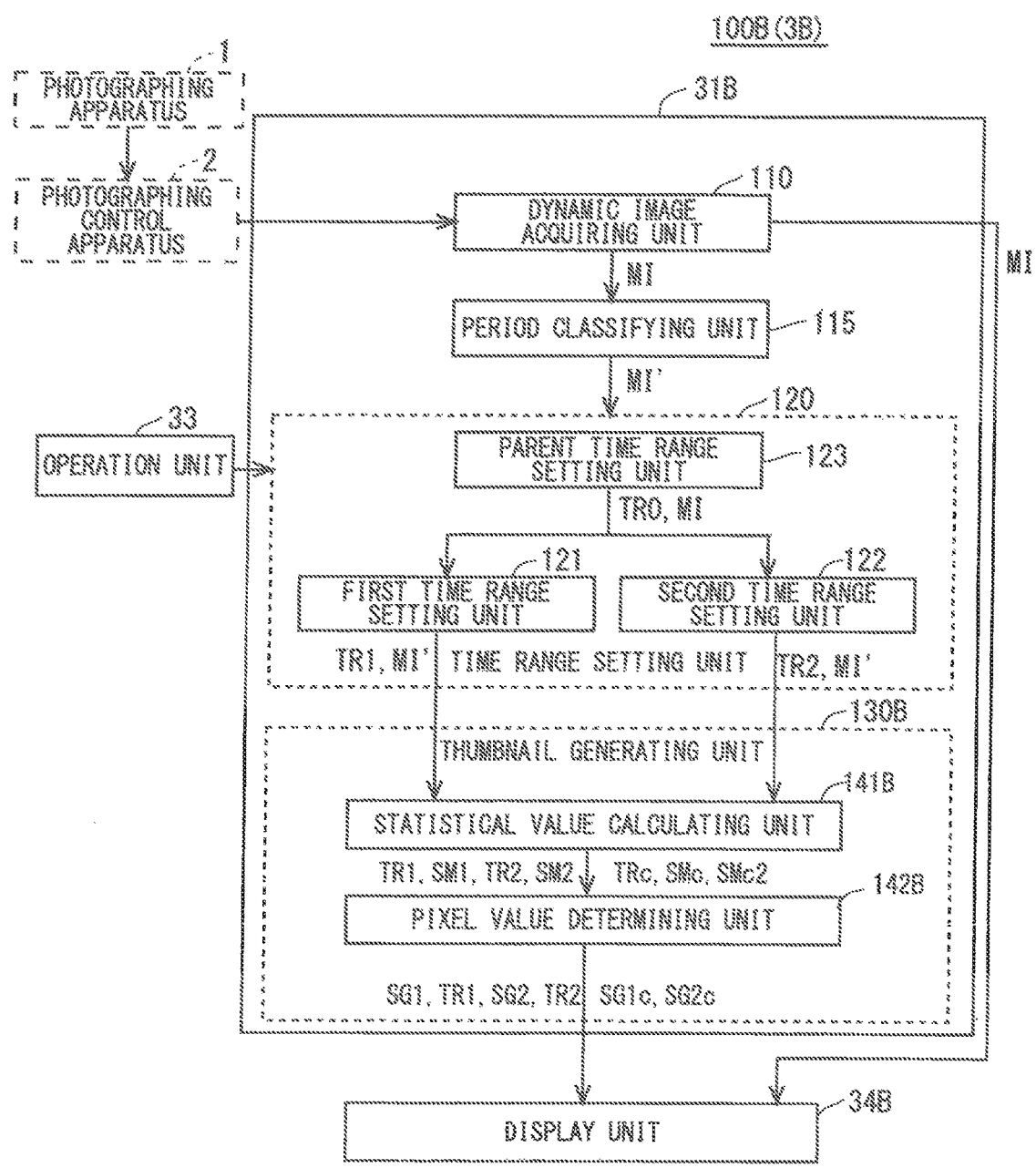
F I G. 2 5

IMAGE PROCESSING APPARATUS FOR ACQUIRING A DYNAMIC IMAGE AND STORAGE MEDIUM

CROSS REFERENCE TO RELATED APPLICATION

This Application is a 371 of PCT/JP2014/062130 filed on May 2, 2014 which, in turn, claimed the priority of Japanese Patent Application No. JP2013-115889 filed on May 31, 2013, both applications are incorporated herein by reference.

TECHNICAL FIELD

The present invention relates to image processing technology for processing a dynamic image obtained by photographing a human body or an animal body.

BACKGROUND ART

In medical settings, an affected part in internal organs, skeletons, and the like is photographed, for example, with X-rays for various tests and diagnoses. Through application of recent digital technology, a dynamic image (an image group including a plurality of frame images) in which movement of an affected part is captured, for example, with X-rays can be acquired relatively easily.

In the recent digital technology, a dynamic image of a subject region including a diagnosis target region can be photographed with use of a semiconductor image sensor such as a flat panel detector (FPD), and thus an attempt to perform pathological analysis and diagnosis based on motion analysis of the diagnosis target region and the like, which cannot be performed in still image photography and diagnosis by conventional X-ray photography, is made. Particularly in dynamic analysis of the chest using X-rays, the following study is conducted; ventilatory information and blood flow information in the lung field are extracted, and dynamic functions related to a density change in the lung field and movement of blood flow at every position are quantitatively analyzed to support diagnosis and/or treatment (CAD for X-ray moving images).

As a method for achieving quantitative analysis described above, technology for analyzing a temporal change based on frame images constituting a dynamic image of the chest to generate analysis information effective in diagnosis has been proposed.

For example, Patent Document 1 discloses technology for separately using filters in such a manner that a high-pass filter is used to perform blood flow analysis and a low-pass filter is used to perform ventilatory analysis to eliminate the effects of density values of blood flow and ventilation on each other to thereby accurately extract ventilation and blood flow using inter-filter differences.

Patent Document 2 discloses technology for sorting frame images depending on whether each of the frame images belongs to an arterial phase or a venous phase to generate integrated images.

Patent Document 3 discloses technology for measuring the positions of left and right portions of the diaphragm and the apical portions of the lungs, acquiring moving amounts, and displaying a graph showing movement based on the moving amounts.

Patent Document 4 discloses technology for calculating a feature amount (period length and/or amplitude) for each period, and displaying a graph showing the feature amount as diagnosis support information.

Furthermore, Patent Document 5 discloses technology for selecting a plurality of important images to display a list thereof as thumbnails, and playing back a moving image through operation to select a thumbnail.

PRIOR ART DOCUMENTS

Patent Document

Patent Document 1: Japanese Patent Application Laid-Open Publication No. 2012-110399
Patent Document 2: Japanese Patent Application Laid-Open Publication No. 2012-005729
Patent Document 3: WO 2006/137294
Patent Document 4: Japanese Patent Application Laid-Open Publication No. 2009-273671
Patent Document 5: Japanese Patent Application Laid-Open Publication No. 2012-011120

SUMMARY OF INVENTION

Problems to be Solved by Invention

The integrated images created in the above-mentioned method disclosed in Patent Document 2 are two time-sharing thumbnail images of the pulmonary arterial phase and the pulmonary venous phase, but the difference per pulsation (cardiac) period cannot be determined.

The graph shown in the above-mentioned method disclosed in Patent Document 3 can be used to visually observe a change in a time direction, but cannot be used to visually identify the difference on frame images.

The graph shown in the above-mentioned method disclosed in Patent Document 4 can be used to display an analysis value per cardiac period, but cannot be used to visually identify the difference on frame images.

The thumbnails displayed in the above-mentioned method disclosed in Patent Document 5 show the difference between dynamic images, but do not show the difference for each period as a target has no periodicity.

Furthermore, in the above-mentioned technology disclosed in Patent Document 1, integrated images using a plurality of frame images, i.e., thumbnail images corresponding to still images, are not created.

As described above, in the above-mentioned technology disclosed in Patent Documents 1 to 5, a temporal change of a two-dimensional space on the frame images cannot be captured, and this makes it difficult to provide perspicuity and to visually observe the change in the time direction.

The present invention has been conceived in view of the above-mentioned matters, and aims to provide image processing technology enabling visual capture of a temporal change of a two-dimensional space on frame images, and immediate selection of a desired time range from an overall time of a dynamic image.

Means for Solving the Problems

In order to solve the above-mentioned problems, an image processing apparatus according to a first aspect of the present invention includes: a dynamic image acquiring unit for acquiring a dynamic image including a plurality of frame images obtained by sequentially photographing, in a time direction, a state of a dynamic period in which a physical state in a body of a human or an animal changes periodically; a time range setting unit for performing time range setting processing including (a1) first time range setting processing to set, in an overall time of the dynamic image, a first time range composed of one or more dynamic periods, and (a2) second time range setting processing to set a second time range in the overall time of the dynamic image; a thumbnail generating unit for performing thumbnail generating processing to generate a first thumbnail image and a second thumbnail image, the first thumbnail image being a still image obtained by performing statistical processing on frame images in the first time range, the second thumbnail image being a still image obtained by performing the statistical processing on frame images in the second time range; and a display unit for displaying the first thumbnail image and the second thumbnail image so that the first thumbnail image and the second thumbnail image are capable of being visually compared with each other.

The invention of a second aspect is the image processing apparatus according to the first aspect, and the second time range setting processing includes processing to set the second time range composed of one or more dynamic periods.

The invention of a third aspect is the image processing apparatus according to the first or second aspect, and the time range setting processing includes parent time range setting processing to set, in the overall time of the dynamic image, a parent time range for setting the first time range and the second time range, and the first time range and the second time range are both included in the parent time range.

The invention of a fourth aspect is the image processing apparatus according to the third aspect, and the parent time range setting processing includes: processing to set one of the first time range and the second time range as a parent time range for hierarchical display; and processing to newly set the parent time range for hierarchical display as the parent time range, the first time range setting processing includes processing to newly set the first time range in the parent time range for hierarchical display, and the second time range setting processing includes processing to newly set the second time range in the parent time range for hierarchical display.

The invention of a fifth aspect is the image processing apparatus according to the third aspect, and the second time range setting processing includes processing to set the second time range so that the second time range is equal to an overall time range of the parent time range.

The invention of a sixth aspect is the image processing apparatus according to the third aspect, and the time range setting processing further includes processing to set the first time range and the second time range so that all time ranges of the first time range and the second time range do not overlap each other, and are continuous.

The invention of a seventh aspect is the image processing apparatus according to the sixth aspect, and the time range setting processing further includes processing to set the first time range and the second time range so that a total time range of the first time range and the second time range matches the parent time range.

The invention of an eighth aspect is the image processing apparatus according to the third aspect, and the time range setting processing includes processing to set the first time range and the second time range so that all time ranges of the first time range and the second time range include the same number of dynamic periods.

The invention of a ninth aspect is the image processing apparatus according to the first aspect, and the thumbnail generating processing includes: statistical value calculating processing to calculate, with respect to the first time range or the second time range, a pixel statistical value for each corresponding pixel among the frame images; and pixel value determining processing to determine a pixel value for the first thumbnail image or the second thumbnail image based on the pixel statistical value.

The invention of a tenth aspect is the image processing apparatus according to the ninth aspect, and the statistical value calculating processing further includes processing to normalize the pixel statistical value by the number of dynamic periods included in the first time range or the second time range with respect to which the pixel statistical value has been calculated.

The invention of an eleventh aspect is the image processing apparatus according to the ninth aspect, and the pixel value determining processing further includes processing to determine the pixel value for the first thumbnail image or the second thumbnail image using a pixel statistical value in a time range for comparison, the time range for comparison including at least one of the first time range and the second time range.

The invention of a twelfth aspect is the image processing apparatus according to the ninth aspect, and the pixel statistical value is any of a maximum value, an average value, a minimum value, and a median value of pixel density calculated with respect to the first time range and the second time range for each corresponding pixel among the frame images.

The invention of a thirteenth aspect is the image processing apparatus according to the third aspect, and the time range setting processing further includes: (a3) statistical value calculating processing to calculate, with respect to a plurality of time ranges included in the parent time range, a plurality of pixel statistical values for each corresponding pixel among the frame images; and (a4) similarity degree calculating processing to calculate a degree of similarity between time ranges adjacent to each other in terms of time in the plurality of time ranges based on the plurality of pixel statistical values calculated with respect to the plurality of time ranges, the first time range setting processing includes processing to set the first time range in the plurality of time ranges based on the degree of similarity, and the second time range setting processing includes processing to set the second time range in the plurality of time ranges based on the degree of similarity.

The invention of a fourteenth aspect is the image processing apparatus according to the first aspect further including an operation unit for receiving setting information set by a user, and the setting information includes information for setting a predetermined time range, the thumbnail generating processing further includes processing to generate a thumbnail image in the predetermined time range indicated by the setting information inputted through the operation unit by performing the statistical processing using frame images in the predetermined time range, and the display unit performs processing to display the thumbnail image in the predetermined time range.

The invention of a fifteenth aspect is the image processing apparatus according to the fourteenth aspect, and the setting information further includes information for setting a hidden time range, and the display unit performs processing to hide the first thumbnail image or the second thumbnail image in a time range included in the hidden time range based on the setting information inputted through the operation unit.

The invention of a sixteenth aspect is the image processing apparatus according to the fourteenth aspect, and the setting information includes information for setting a predetermined number of time ranges of the first time range and the second time range as an aggregate time range, the predetermined number being two or more, the thumbnail generating processing further includes processing to generate a thumbnail image in the aggregate time range indicated by the setting information inputted through the operation unit by performing the statistical processing using frame images in the aggregate time range, and the display unit performs: processing to hide a predetermined number of thumbnail images in time ranges included in the aggregate time range; and processing to display the thumbnail image in the aggregate time range.

The invention of a seventeenth aspect is the image processing apparatus according to the first aspect further including an operation unit for receiving setting information set by a user, and the setting information includes information for setting one of the first thumbnail image and the second thumbnail image as a thumbnail image for moving image comparison, and the display unit performs processing to play back a dynamic image corresponding to the thumbnail image for moving image comparison based on the setting information inputted through the operation unit.

The invention of a eighteenth aspect is the image processing apparatus according to any one of the first to seventeenth aspects, and the dynamic period includes a cardiac period or a respiratory period.

The invention of a nineteenth aspect is a computer-readable non-transitory storing medium storing a program executed by a computer included in an image processing apparatus according to any one of the first to eighteenth aspects.

Effects of Invention

The image processing apparatus according to the first to eighteenth aspects includes: the thumbnail generating unit for performing the thumbnail generating processing to generate the first thumbnail image, which is the still image obtained by performing the statistical processing on a dynamic image in the first time range set in multiples of the dynamic period (including one or more dynamic periods), using the frame images in the first time range, and generate the second thumbnail image, which is the still image obtained by performing the statistical processing on a dynamic image in the second time range, using the frame images in the second time range; and the display unit for displaying the first thumbnail image and the second thumbnail image so that the first thumbnail image and the second thumbnail image can visually be compared with each other. That is to say, since the first thumbnail image and the second thumbnail image, which show the dynamic images as the still images, are displayed so as to be visually compared with each other, the user can understand the feature into which the dynamic images in the first time range and the second time range are aggregated at a glance by viewing the first thumbnail image and the second thumbnail image without viewing the dynamic image as a whole. As a result, the difference per first time range and second time range in the dynamic image can properly and efficiently be seen. This allows the user to immediately determine and select the desired time range based on the difference per first time range and second time range, leading to improvement in efficiency of diagnosis. For the above-mentioned reasons, dynamic diagnosis can properly and efficiently be made.

According to the image processing apparatus according to the second aspect, the second time range setting processing includes the processing to set the second time range composed of one or more dynamic periods. That is to say, the first thumbnail image and the second thumbnail image are generated in multiples of the dynamic period (including one or more dynamic periods) by setting both the first time range and the second time range in multiples of the dynamic period. As a result, the time ranges can be adjusted in multiples of the dynamic period, and thus the difference between them can properly be compared with each other.

According to the image processing apparatus according to the third aspect, the time range setting processing includes the parent time range setting processing to set, in the overall time of the dynamic image, the parent time range for setting the first time range and the second time range, and the first time range and the second time range are both included in the parent time range. That is to say, by setting the parent time range as a target for analysis, the first time range and the second time range included in the parent time range can properly be set. As a result, the first thumbnail image and the second thumbnail image suitable for comparison can be generated.

According to the image processing apparatus according to the fourth aspect, the parent time range setting processing includes: processing to set one of the first time range and the second time range as the parent time range for hierarchical display; and processing to newly set the parent time range for hierarchical display as the parent time range, the first time range setting processing includes processing to newly set the first time range in the parent time range for hierarchical display, and the second time range setting processing includes processing to newly set the second time range in the parent time range for hierarchical display. That is to say, by newly setting the first time range or the second time range as a new parent time range (parent time range for hierarchical display), once-divided time ranges can further be divided into smaller parts. As a result, further-divided thumbnail images can be displayed, and thus the thumbnail images can specifically be compared with each other for determination.

According to the image processing apparatus according to the fifth aspect, the second time range setting processing includes processing to set the second time range so that the second time range is equal to the overall time range of the parent time range. That is to say, by setting the second time range as the parent time range, the first time range can be set as a part of the second time range to be focused on. As a result, the first thumbnail image can be displayed while focusing on the part of the second thumbnail image to be focused on. A time range with any abnormality can thus be displayed as the first thumbnail image, for example.

According to the image processing apparatus according to the sixth aspect, the time range setting processing further includes processing to set the first time range and the second time range so that all the time ranges of the first time range and the second time range do not overlap each other, and are continuous. That is to say, since the first time range and the second time range are continuous in terms of time, thumbnail images can be generated in the continuous time ranges with no omission. As a result, the thumbnail images in a continuous time can be displayed in parallel to each other for check in consideration of a time direction. Therefore, in a case where an abnormal part appears and then disappears, for example, diagnosis can be made on a time process thereof.

According to the image processing apparatus according to the seventh aspect, the time range setting processing further includes processing to set the first time range and the second time range so that the total time range of the first time range and the second time range matches the parent time range. That is to say, throughout the parent time range as a target for analysis, the thumbnail images can be generated in the continuous time ranges with no omission. As a result, the thumbnail images in the continuous time throughout the range as a target for analysis can be displayed in parallel to each other for check in consideration of the time direction. Therefore, in a case where the abnormal part appears and then disappears, for example, diagnosis can be made on the time process thereof throughout the range as a target for analysis.

According to the image processing apparatus according to the eighth aspect, the time range setting processing includes processing to set the first time range and the second time range so that all the time ranges of the first time range and the second time range include the same number of dynamic periods. That is to say, since there is no difference in number of dynamic periods between time ranges, time ranges suitable for comparison can be set. As a result, the thumbnail images can properly be compared with each other independently of the number of dynamic periods.

According to the image processing apparatus according to the ninth aspect, the thumbnail generating processing includes: the statistical value calculating processing to calculate, with respect to the first time range or the second time range, the pixel statistical value for each corresponding pixel among the frame images; and the pixel value determining processing to determine the pixel value for the first thumbnail image or the second thumbnail image based on the pixel statistical value. That is to say, the pixel statistical value in each time range can be viewed as a still image. By generating the thumbnail images using the common pixel statistical value (e.g., a maximum value and a total value), the difference in feature between dynamic images in respective time ranges can easily be checked through comparison.

According to the image processing apparatus according to the tenth aspect, the statistical value calculating processing further includes processing to normalize the pixel statistical value by the number of dynamic periods included in the first time range or the second time range with respect to which the pixel statistical value has been calculated. In a case where the first thumbnail image and the second thumbnail image are compared with each other, if the pixel statistical value is a total value, the pixel statistical value per unit period can be obtained by dividing (normalizing) the total value by the number of dynamic periods. That is to say, in a case where the number of dynamic periods varies between thumbnail images, thumbnail images that are equivalent to each other when being compared with each other can be generated. As a result, the thumbnail images can properly be compared with each other independently of the number of dynamic periods.

According to the image processing apparatus according to the eleventh aspect, the pixel value determining processing further includes processing to determine the pixel value for the first thumbnail image or the second thumbnail image using the pixel statistical value in the time range for comparison including at least one of the first time range and the second time range. That is to say, since the pixel value for the first thumbnail image or the second thumbnail image is determined using the pixel statistical value in the time range for comparison, spatial differences between thumbnail images (in a time direction of the dynamic image) can be associated with each other in the two-dimensional space on the thumbnail images, and viewed and compared with each other. This facilitates understanding of a time-space change of the dynamic image. In addition, the abnormal part can be clarified, and thus dynamic diagnosis can properly and efficiently be made.

According to the image processing apparatus according to the twelfth aspect, the pixel statistical value is any of the maximum value, the average value, the minimum value, and the median value of the pixel density for each corresponding pixel among the frame images. Therefore, in a case where the maximum value of the pixel density is used as the pixel statistical value, for example, if the maximum value is small, a low pixel density is reflected. This produces the effects that blood flow can be presumed to be poor.

According to the image processing apparatus according to the thirteenth aspect, the time range setting processing further includes: (a3) the statistical value calculating processing to calculate, with respect to the plurality of time ranges included in the parent time range, the plurality of pixel statistical values for each corresponding pixel among the frame images; and (a4) the similarity degree calculating processing to calculate the degree of similarity between time ranges adjacent to each other in terms of time in the plurality of time ranges based on the plurality of pixel statistical values calculated with respect to the plurality of time ranges, the first time range setting processing includes processing to set the first time range in the plurality of time ranges based on the degree of similarity, and the second time range setting processing includes processing to set the second time range in the plurality of time ranges based on the degree of similarity. For example, time ranges can be grouped based on a determination criterion that the degree of similarity between time ranges is higher than a predetermined value, and the first time range and the second time range can be set based on the grouping. That is to say, by generating a thumbnail image in a time range composed of time ranges with a high degree of similarity, classification on whether a time range to be specifically analyzed is included can efficiently be performed. In addition, by narrowing down time ranges to the time ranges with the high degree of similarity, the number of thumbnail images to be visually compared with each other can be reduced.

According to the image processing apparatus according to the fourteenth aspect, the thumbnail generating processing further includes processing to generate the thumbnail image in the predetermined time range indicated by the setting information inputted through the operation unit by performing the statistical processing using the frame images in the predetermined time range, and the display unit performs processing to display the thumbnail image in the predetermined time range. As a result, when the user inputs the predetermined time range through the operation unit, the thumbnail image in the predetermined time range is displayed.

According to the image processing apparatus according to the fifteenth aspect, the display unit performs processing to hide the first thumbnail image or the second thumbnail image in the time range included in the hidden time range based on the setting information inputted through the operation unit. For example, in a case where there are a plurality of first thumbnail images and second thumbnail images to be compared with each other for analysis, the user can designate a thumbnail image not required to be displayed to hide the thumbnail image. As a result, only the thumbnail image to be focused on can be displayed. The display unit can thus effectively use a space on the display.

According to the image processing apparatus according to the sixteenth aspect, the thumbnail generating processing further includes processing to generate the thumbnail image in the aggregate time range indicated by the setting information inputted through the operation unit by performing the statistical processing using the frame images in the aggregate time range, and the display unit performs: processing to hide the predetermined number of thumbnail images in the time ranges included in the aggregate time range; and processing to display the thumbnail image in the aggregate time range. That is to say, in a case where there are a plurality of thumbnail images to be compared with each other for analysis, time ranges determined to be equivalent to each other through comparison can be integrated into a time range for a single thumbnail image. This can reduce the number of thumbnail images not required to be compared. The display unit can thus effectively use the space on the display.

According to the image processing apparatus according to the seventeenth aspect, the display unit performs processing to play back the dynamic image corresponding to the thumbnail image for moving image comparison based on the setting information inputted through the operation unit. This allows the user to perform operation to compare the thumbnail images (still images) and operation to view the dynamic image in parallel to each other. As a result, dynamic diagnosis can properly and efficiently be made.

According to the image processing apparatus according to the eighteenth aspect, the dynamic period includes the cardiac period or the respiratory period. As a result, a cardiac period or a respiratory period (time period) with any abnormality can be specified from the thumbnail images, and thus dynamic diagnosis can be made only in the time period with the abnormality. Thus, time required for dynamic diagnosis can be reduced, and dynamic diagnosis can properly and efficiently be made.

According to the program according to the nineteenth aspect, effects that are the same as those obtained in the invention according to the first to eighteenth aspects can be obtained.

The objects, features, aspects and advantages of the present invention will become more apparent from the following detailed description and the accompanying drawings.

BRIEF DESCRIPTION OF DRAWINGS

FIG. 1 is a diagram showing an overall configuration of a radiographic dynamic image photographing system 100 according to Embodiment 1.

FIG. 2 is a diagram for explaining problems in blood flow dynamic diagnosis.

FIG. 5 is a schematic diagram for explaining cardiac period acquiring processing.

FIG. 7 is a schematic diagram for explaining time range setting processing.

FIG. 8 is a schematic diagram for explaining the time range setting processing.

FIG. 14 is a schematic diagram for explaining the time range setting processing.

FIG. 16 is a schematic diagram for explaining thumbnail generating processing.

FIG. 19 is a schematic diagram for explaining the thumbnail display processing.

FIG. 20 is a schematic diagram for explaining the thumbnail display processing.

FIG. 23 is a block diagram showing a functional configuration of a time range setting unit 120A according to Embodiment 2.

FIG. 25 is a block diagram showing a functional configuration of an image processing apparatus 3B according to Embodiment 3.

DESCRIPTION OF EMBODIMENTS

Figure 3:
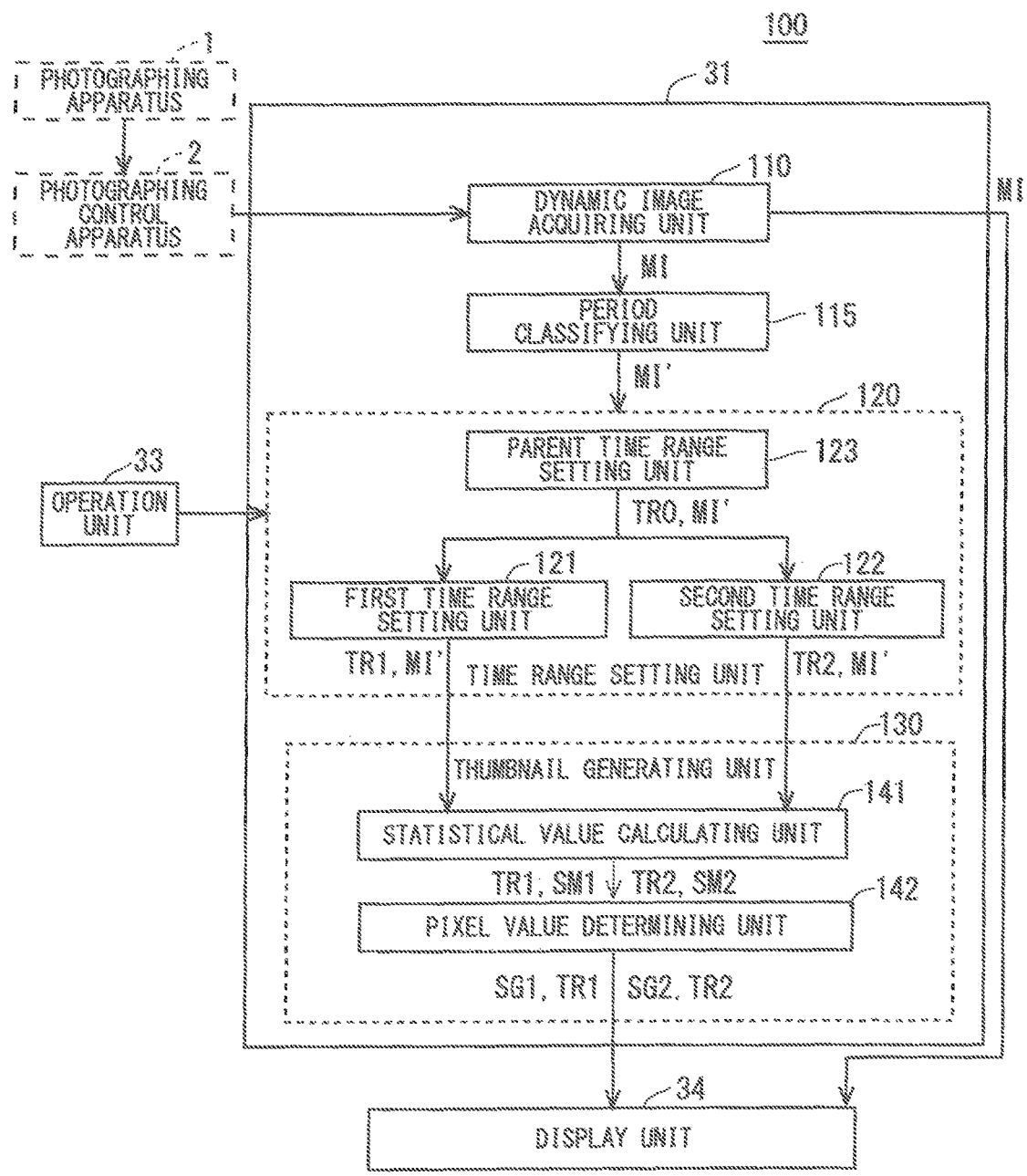
FIG. 3 is a block diagram showing a functional configuration of an image processing apparatus 3 according to Embodiment 1.

A term "thumbnail image" in the present description hereinafter refers to a still image obtained by performing statistical processing on a plurality of image frames as a part of a dynamic image in a predetermined time range.

1. Embodiment 1

A radiographic dynamic image photographing system according to Embodiment 1 of the present invention is described below.

<1-1. Overall Configuration of Radiographic Dynamic Image Photographing System>

The radiographic dynamic image photographing system according to Embodiment 1 photographs a radiographic image of a human body or an animal body as a subject in a situation in which a physical state of a target region of the subject changes periodically over time.

FIG. 1 is a diagram showing an overall configuration of the radiographic dynamic image photographing system according to Embodiment 1. As shown in FIG. 1, a radiographic dynamic image photographing system 100 includes a photographing apparatus 1, a photographing control apparatus 2 (photographing console), an image processing apparatus 3 (diagnosis console), and an electrocardiograph 4. The photographing apparatus 1 and the electrocardiograph 4 are connected to the photographing control apparatus 2 by a communication cable or the like, and the photographing control apparatus 2 and the image processing apparatus 3 are connected to each other through a communication network NT such as a local area network (LAN). These apparatuses constituting the radiographic dynamic image photographing system 100 comply with the digital image and communications in medicine (DICOM) standard, and communicate with each other in accordance with the DICOM standard.

<1-1-1. Configuration of Photographing Apparatus 1>

The photographing apparatus 1 is configured, for example, by an X-ray photographing apparatus or the like, and photographs dynamics of the chest of a subject M involved in respiration. The dynamics are photographed by sequentially acquiring a plurality of images over time while repeatedly irradiating the chest of the subject M with radiation such as X-rays. A series of images acquired through the continuous photography is referred to as a dynamic image. The images constituting the dynamic image are each referred to as a frame image.

As shown in FIG. 1, the photographing apparatus 1 includes an irradiation unit (a radiation source) 11, an irradiation control device 12, an imaging unit (a radiation detecting unit) 13, and a reading control device 14.

The irradiation unit 11 irradiates the subject M with radiation (X-rays) under control of the irradiation control device 12. Illustrated as an example is a system for a human body, and the subject M corresponds to a test target. The subject M is hereinafter also referred to as a "test subject".

The irradiation control device 12 is connected to the photographing control apparatus 2, and controls the irradiation unit 11 based on an irradiation condition inputted from the photographing control apparatus 2 for radiography.

The imaging unit 13 is configured by a semiconductor image sensor such as an FPD, and converts radiation having been emitted from the irradiation unit 11 and having passed through the test subject M into an electrical signal (image information).

The reading control device 14 is connected to the photographing control apparatus 2. The reading control device 14 controls switching units of pixels of the imaging unit 13 based on an image reading condition inputted from the photographing control apparatus 2 to switch reading of the electrical signals stored in the pixels, and reads the electrical signals stored in the imaging unit 13 to acquire image data. The reading control device 14 then outputs the acquired image data (frame images) to the photographing control apparatus 2. The image reading condition includes, for example, a frame rate, a frame interval, a pixel size, and an image size (a matrix size). The frame rate is the number of frame images acquired per second, and matches a pulse rate. The frame interval is a time from the start of an operation to acquire one frame image to the start of an operation to acquire the next frame image in continuous photography, and matches a pulse interval.

The irradiation control device 12 and the reading control device 14 are herein connected to each other, and exchange synchronizing signals with each other to synchronize an irradiation operation and an image reading operation with each other.

<1-1-2. Configuration of Photographing Control Apparatus 2>

The photographing control apparatus 2 outputs the irradiation condition and the image reading condition to the photographing apparatus 1 to control radiography and a radiographic image reading operation performed by the photographing apparatus 1, and also displays a dynamic image acquired by the photographing apparatus 1 so that a radiographer can check positioning and whether the image is an image suitable for diagnosis.

As shown in FIG. 1, the photographing control apparatus 2 includes a control unit 21, a storage unit 22, an operation unit 23, a display unit 24, and a communication unit 25, and these units are connected to one another by a bus 26.

The control unit 21 is configured by a central processing unit (CPU), a random access memory (RAM), and the like. The CPU of the control unit 21 reads a system program and various processing programs stored in the storage unit 22 in response to an operation of the operation unit 23 to develop them in the RAM, and performs various types of processing such as photographing control processing, which is described below, in accordance with the developed programs to perform centralized control of an operation of each unit of the photographing control apparatus 2 and an operation of the photographing apparatus 1.

The storage unit 22 is configured by a nonvolatile semiconductor memory, a hard disk, and the like. The storage unit 22 stores various programs to be executed by the control unit 21 and parameters required for the programs to perform processing, or data on processing results, and the like.

The operation unit 23 includes a keyboard including cursor keys, numeric keys, and various function keys, and a pointing device such as a mouse, and outputs an instruction signal inputted through a key operation made on the keyboard, a mouse operation, or a touch panel to the control unit 21.

The display unit 24 is configured by a monitor such as a color liquid crystal display (LCD), and displays an input instruction from the operation unit 23, data, and the like in accordance with an instruction of a display signal inputted from the control unit 21.

The communication unit 25 includes a LAN adapter, a modem, a terminal adapter (TA), and the like, and controls data transmission and reception with each device connected to the communication network NT.

<1-1-3. Configuration of Image Processing Apparatus 3>

The image processing apparatus 3 acquires a dynamic image transmitted from the photographing apparatus 1 through the photographing control apparatus 2, and displays an image to be used by a doctor or the like to make diagnosis through reading.

As shown in FIG. 1, the image processing apparatus 3 includes a control unit 31, a storage unit 32, an operation unit 33, a display unit 34, and a communication unit 35, and these units are connected to one another by a bus 36.

The control unit 31 is configured by a CPU, a RAM, and the like. The CPU of the control unit 31 reads a system program and various processing programs stored in the storage unit 32 in response to an operation of the operation unit 33 to develop them in the RAM, and performs various types of processing in accordance with the developed programs to perform centralized control of an operation of each unit of the image processing apparatus 3 (described in detail below).

The storage unit 32 is configured by a nonvolatile semiconductor memory, a hard disk, and the like. The storage unit 32 stores various programs to be executed by the control unit 31 and parameters required for the programs to perform processing, or data on processing results, and the like. For example, the storage unit 32 stores an image processing program for performing image processing, which is described below. These various programs are stored in the form of readable program codes, and the control unit 31 sequentially performs operations in accordance with the program codes.

The operation unit 33 includes a keyboard including cursor keys, numeric keys, and various function keys, and a pointing device such as a mouse, and outputs an instruction signal inputted through a key operation made on the keyboard, a mouse operation, or a touch panel to the control unit 31.

The display unit 34 is configured by a monitor such as a color LCD, and displays an input instruction from the operation unit 33, data, and a display image, which is described below, in accordance with an instruction of a display signal inputted from the control unit 31.

The communication unit 35 includes a LAN adapter, a modem, a TA, and the like, and controls data transmission and reception with each device connected to the communication network NT.

<1-1-4. Configuration of Electrocardiograph 4>

Although the electrocardiograph 4 is shown to be apart from the test subject M in FIG. 1, each electrode terminal of the electrocardiograph 4 is actually attached to the test subject M to output an electrocardiographic waveform of the test subject M as a digital signal.

As shown in FIG. 1, the electrocardiograph 4 includes a phase detecting unit 41, and the phase detecting unit 41 detects, in response to a control signal from the CPU of the control unit 21, a phase of a heart rate of the subject M as base information for synchronizing a photographing operation performed by the imaging apparatus 1.

<1-2. Problems in Blood Flow Dynamic Diagnosis>

Problems in blood flow dynamic diagnosis are described as a premise of description of the details of the image processing apparatus 3 in the present embodiment.

FIG. 2 is a diagram for explaining the problems in blood flow dynamic diagnosis. Part (a) of FIG. 2 is a schematic diagram illustrating, in a time direction, a blood flow dynamic image (frame images IG) obtained after blood flow analysis is performed on frame images constituting a dynamic image, and part (b) of FIG. 2 is a schematic diagram illustrating a thumbnail image SGo obtained by superimposing the frame images IG constituting the blood flow dynamic image onto one another as a single still image for display.

As illustrated in part (a) of FIG. 2, in blood flow dynamic diagnosis, a doctor/radiologist searches the dynamic image for the absence, shortage, and timing delay of blood flow to find vascular occlusion. Diagnosis can be made using the dynamic image, for example, by finding the absence of blood flow in a region R1 of a frame image IG at time t2. The presence or absence of noise and a direction of blood flow are also checked.

It is, however, difficult to visually determine (diagnose) a normal portion and an abnormal portion from the dynamic image. This means that viewing of the dynamic image has various problems as it takes a long time to make diagnosis, there is a risk of overlooking, and it is difficult to understand an overall view of the dynamic image in a two-dimensional space, for example.

On the other hand, as illustrated in part (b) of FIG. 2, there is a method of superimposing images onto one another using a representative value, such as a total value and a maximum value, obtained through statistical processing for each corresponding pixel in a time direction of a blood flow dynamic image to display a single still image (thumbnail image) SGo. Rough diagnosis can be made using the still image, for example, by finding weak blood flow in a region R2. Since the blood flow dynamic image is full of noise and varies among individuals, it is necessary to search the thumbnail image SGo for roughness and/or deficiency, and find a delay and/or lack through comparison using the dynamic image to analyze and limit the phenomenon. As described above, viewing of a single thumbnail image SGo facilitates understanding of a user, such as a doctor, of the overall view of the blood flow dynamic image in the two-dimensional space, and allows the user to comprehensively understand the blood flow dynamic image and to check the roughness for a lack and/or an increase or a decrease of blood flow.

That is to say, as a method for making diagnosis on dynamic blood flow, the user views a still image having undergone the statistical processing to understand spatial distribution to thereby estimate an abnormal position, and then views the dynamic image to check whether the target portion is abnormal in terms of time. Since there are many noise factors in blood flow analysis, it is important to make full use of the still image and the dynamic image for diagnosis as described above.

With a single thumbnail image SGo as illustrated in part (b) of FIG. 2, however, analysis in a time direction to understand the difference in blood flow per cardiac period or per particular time range (arrhythmia), photographing variable noise, and the like cannot be performed as a plurality of thumbnail images are not displayed. It is therefore necessary to observe the difference per cardiac period or per particular time range using the dynamic image, and there are problems in that it takes a long time to observe the difference, and efficiency of diagnosis is extremely reduced.

Under such consideration, it is desirable to divide the dynamic image for each cardiac period or particular time range to display thumbnail images.

In the present invention, the dynamic image is divided for each cardiac period or particular time range to generate a plurality of thumbnail images, and, as a result, the user can compare still images to find the difference of the dynamic image between cardiac periods or particular time ranges, and can easily select a desired cardiac period or a particular time range from an overall time of the dynamic image.

The image processing apparatus 3 in Embodiment 1 is described in detail below.

<1-3. Specific Configuration of Image Processing Apparatus 3>

The image processing apparatus 3 of the radiographic dynamic image photographing system 100 in Embodiment 1 of the present invention divides the dynamic image for each cardiac period or particular time range to display thumbnail images SG, and, as a result, dynamic diagnosis can properly and efficiently be made.

A functional configuration achieved by the image processing apparatus 3 is described below.

<1-3-1. Functional Configuration of Image Processing Apparatus 3>

FIG. 3 shows a functional configuration achieved by the control unit 31 through operation of the CPU and the like in accordance with various programs in the image processing apparatus 3 of the radiographic dynamic image photographing system 100, along with other configurations. The image processing apparatus 3 in the present embodiment uses a dynamic image obtained by photographing the chest mainly including the heart and both lungs.

The control unit 31 mainly includes a dynamic image acquiring unit 110, a period classifying unit 115, a time range setting unit 120, and a thumbnail generating unit 130.

Although the following description is made on the assumption that the functional configuration of the control unit 31 as shown in FIG. 3 is achieved through execution of a program installed in advance, the functional configuration may be achieved by a dedicated hardware configuration.

Details of processing performed by the dynamic image acquiring unit 110, the period classifying unit 115, the time range setting unit 120, and the thumbnail generating unit 130 are sequentially described with reference to FIG. 3.

<1-3-1-1. Dynamic Image Acquiring Unit 110>

The dynamic image acquiring unit 110 acquires a dynamic image including a plurality of frame images obtained by the reading control device 14 of the photographing apparatus 1 sequentially photographing, in a time direction, a state of a dynamic period in which a physical state in a body of the test subject M changes periodically. The dynamic period in the present embodiment is a cardiac period. That is to say, as shown in FIG. 3, the photographing control apparatus 2 is disposed between the photographing apparatus 1 and the image processing apparatus 3, and detected data (a plurality of frame images MI) stored in the storage unit 22 of the photographing control apparatus 2 is output to the communication unit 35 of the image processing apparatus 3 through the communication unit 25.

Figure 4:
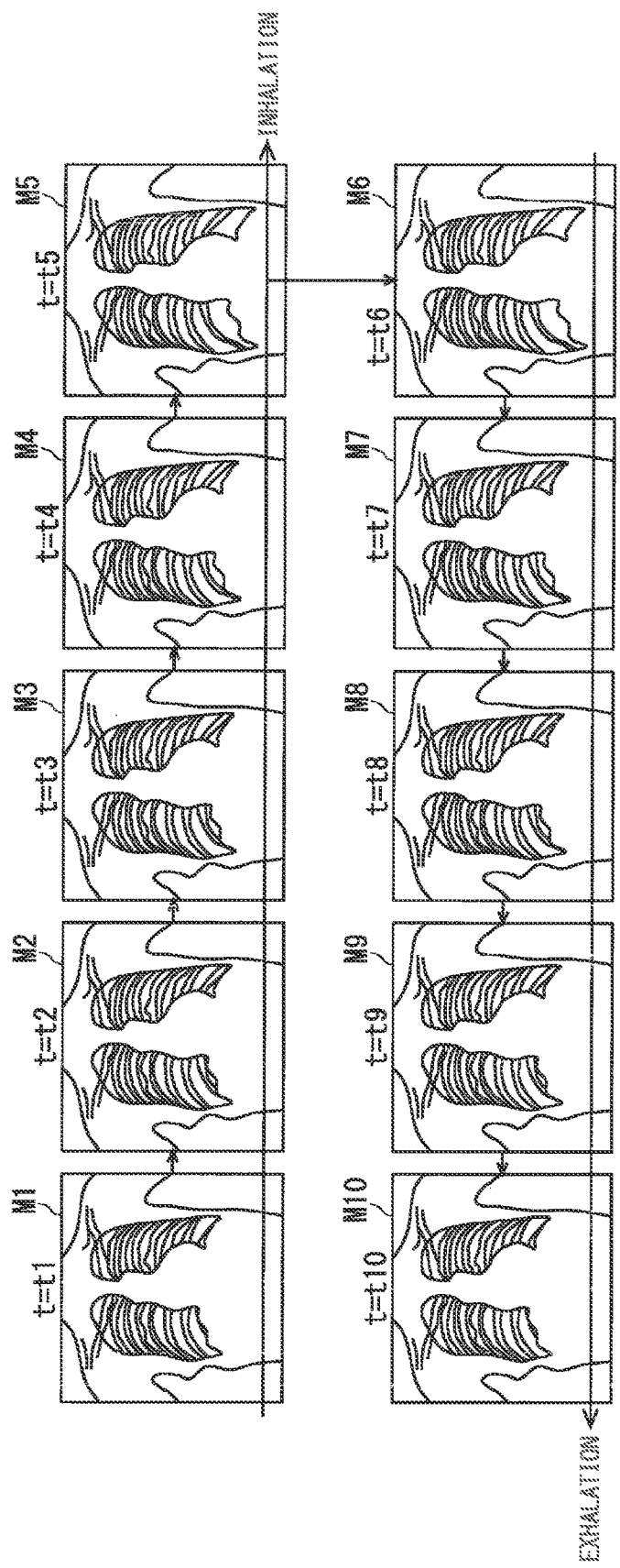
FIG. 4 is a diagram illustrating a dynamic image obtained through radiographic dynamic image photography.

FIG. 4 is a diagram illustrating a dynamic image obtained, as for dynamics of the chest of the subject M involved in respiration, through radiographic dynamic image photography. As illustrated in FIG. 4, frame images M1 to M10 (MI) acquired by the dynamic image acquiring unit 110 are images obtained by continuously photographing one period of the respiratory cycle at constant photographing timings. Specifically, images photographed at photographing timings indicated by time t=t1, t2, t3, . . . , and t10 correspond to the frame images M1, M2, M3, . . . , and M10, respectively.

<1-3-1-2. Period Classifying Unit 115>

In a case where the blood flow dynamic image in which periodic dynamics (blood flow) are captured is converted into still images (thumbnail images) SG for display, the time range is separated for each cardiac period to generate the thumbnail images SG. As a result, the thumbnail images SG can be generated so that the frame images MI constituting the time range show periodic movement with no difference for each phase.

The time range separated for each cardiac period can herein start with a cardiac output phase. This is a timing at which blood starts to flow from the heart to blood vessels, and the dynamic image can be captured in the order of going and returning of blood flow to and from the entire lungs. On the other hand, the time range can start with a cardiac input phase, and, in this case, the dynamic image can be captured in the order of storing and discharging of blood flow in and out of the heart. As a result, in a case where the dynamic image, which is described below, is played back, the dynamic image can be observed from a phase of a frame image to be focused on the most by the user by playing back and displaying the dynamic image from the same time.

As first preprocessing to generate the thumbnail images SG, the period classifying unit 115 detects cardiac periods in the test subject M (body) synchronized with photographing time at which the frame images MI acquired by the dynamic image acquiring unit 110 have been photographed, and classifies the frame images MI into the cardiac periods. The period classifying unit 115 outputs frame images MI' obtained after classification into the cardiac periods to the time range setting unit 120.

Cardiac period acquiring processing performed by the period classifying unit 115 to detect the cardiac periods of the test subject M is described below.

<1-3-1-2-1. Cardiac Period Acquiring Processing>

The cardiac period acquiring processing is processing to calculate the amount of movement of the cardiac wall using a photographed image acquired by the dynamic image acquiring unit 110 to acquire the cardiac periods. Specifically, a change of the cardiac wall is detected from the dynamic image to detect a phase of pulsation of the heart at a timing at which each frame image is photographed. The cardiac periods are determined from the phase of pulsation of the heart.

Various known techniques can be used as a technique for detecting a contour of the heart from each of the frame images MI, and, for example, a technique of detecting the contour of the heart by matching, using a model showing the shape of the heart (heart model), feature points in an X-ray image with feature points in the heart model (for example, see "Image feature analysis and computer-aided diagnosis in digital radiography: Automated analysis of sizes of heart and lung in chest images", Nobuyuki Nakamori et al., Medical Physics, Volume 17, Issue 3, May, 1990, pp. 342-350) can be used.

FIG. 5 is a schematic diagram illustrating the contour of the heart (cardiac wall) extracted from each frame image. As illustrated in parts (a) to (c) of FIG. 5, cardiac walls HL1 to HL3 are extracted based on frame images.

As illustrated in FIG. 5, a change of the width of the heart is used as an example of the change of the cardiac wall HLI captured in the dynamic image. That is to say, parts (a) to (c) of FIG. 5 illustrate how the width of the heart increases from w1 to w3 during expansion of the heart.

The cardiac periods can be detected by detecting the contour of the heart HL1 from each frame image using the above-mentioned method and the like to detect the width of the heart.

Figure 6:
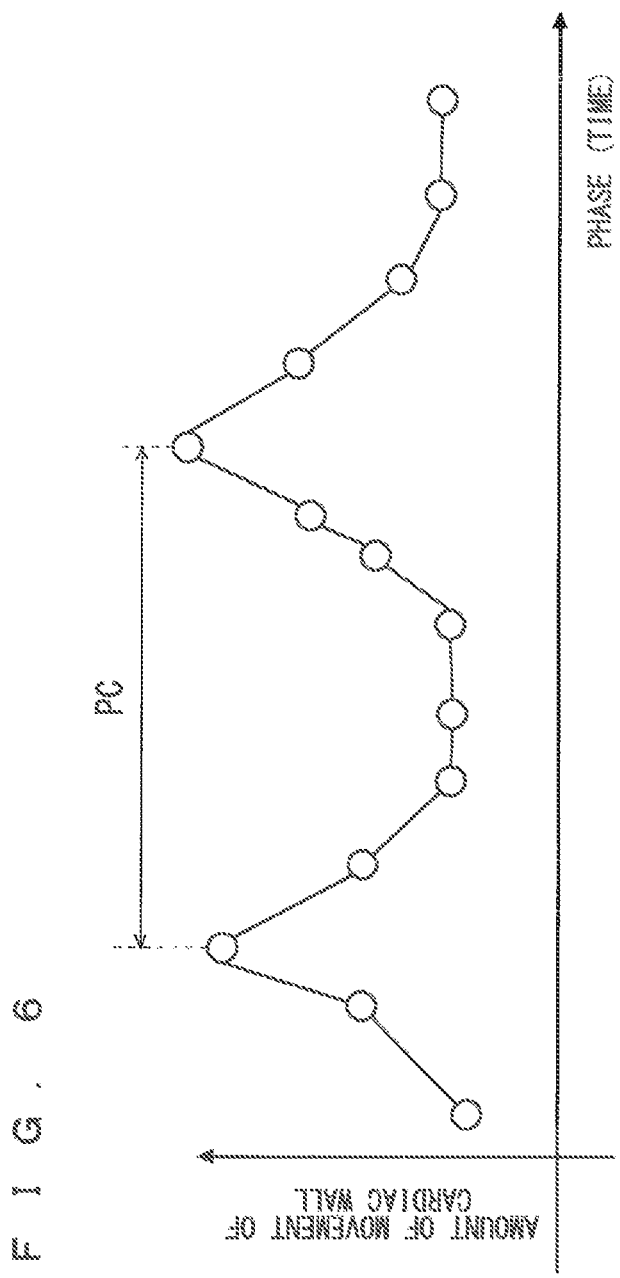
FIG. 6 is a schematic diagram for explaining the cardiac period acquiring processing.

FIG. 6 is a schematic diagram showing the relationship between photographing time and the width of the heart (the amount of movement of the cardiac wall) in frame images constituting a dynamic image. In FIG. 6, the horizontal axis represents time, the vertical axis represents the width of the heart, and circles represent values of the detected width of the heart.

Letting the width of the heart obtained at time t be Hwt and the width of the heart obtained at time t+1 be Hwt+1, if (Hwt+1−Hwt)≥0 is satisfied, a frame image captured at time t is classified as an image during expansion of the heart, and, if (Hwt+1−Hwt)<0 is satisfied, the frame image captured at time t is classified as an image during contraction of the heart.

As described above, detection of a change of the width of the heart, namely, the cardiac wall, allows classification into expansion and contraction of the heart, enabling detection of a phase of pulsation of the heart.

As described above, the period classifying unit 115 can detect the cardiac periods PC based on movement of the cardiac wall captured in the dynamic image, and classify the frame images MI into the cardiac periods PC to obtain the frame images MI' after classification into the cardiac periods PC.

The cardiac period acquiring processing may not be performed in the above-mentioned method, and the cardiac periods PC may be acquired using results acquired from the phase detecting unit 41 (see FIG. 1) of the electrocardiograph 4. This can be achieved by the phase detecting unit 41 of the electrocardiograph 4 performing a detecting operation in synchronization with a photographing operation performed by the photographing apparatus 1.

<1-3-1-3. Time Range Setting Unit 120>

As second preprocessing to generate the thumbnail images SG, the time range setting unit 120 (time range setting processing) includes (a1) a first time range setting unit 121 (first time range setting processing) to set a first time range TR1 in the overall time of the dynamic image in multiples of the cardiac period PC and (a2) a second time range setting unit 122 (second time range setting processing)

to set a second time range TR2 in the overall time of the dynamic image (see FIG. 3). In the second time range setting processing, it is not necessary to set the second time range TR2 in multiples of the cardiac period PC (time composed of one or more cardiac periods PC), but it is preferable to set the second time range TR2 in multiples of the cardiac period PC.

The first time range TR1 refers to a single time range. The second time range TR2 refers to at least one time range (a single time range or a plurality of time ranges).

In a case where the first time range TR1 and the second time range TR2 are set in multiples of the cardiac period PC, the first time range TR1 and the second time range TR2 can easily be set using the frame images MI' obtained by the period classifying unit 115 through classification into the cardiac periods. The first time range TR1 and the second time range TR2 may be set with use of the operation unit 23.

FIGS. 7 to 13 are schematic diagrams for explaining the time range setting processing. A method for generating a thumbnail image SG1 in the first time range TR1 and a thumbnail image SG2 in the second time range TR2 illustrated in FIGS. 7 to 13 is described in detail below.

FIG. 7 is a schematic diagram for explaining the time range setting processing. Part (a) of FIG. 7 illustrates an example of the second time range TR2, and part (b) of FIG. 7 illustrates an example of the first time range TR1. A lower side of an image display block illustrated in part (a) of FIG. 7 represents an overall time TA of the dynamic image.

As illustrated in FIG. 7, the first time range setting unit 121 (first time range setting processing) of the time range setting unit 120 sets the first time range TR1 (see part (b) of FIG. 7), and the second time range setting unit 122 (second time range setting processing) of the time range setting unit 120 sets the second time range TR2 (see part (a) of FIG. 7). In the (basic) time range setting processing illustrated in FIG. 7, the first time range TR1 and the second time range TR2 may or may not overlap each other, and the second time range TR2 may or may not be set in multiples of the cardiac period PC.

Time range setting processing (1) to (5) performed by imposing various restrictions on the (basic) time range setting processing illustrated in FIG. 7 is described below with reference to FIGS. 8 to 15.

<1-3-1-3-1. Time Range Setting Processing (1)>

The time range setting processing (1) includes parent time range setting processing (a parent time range setting unit 123) to set, in the overall time of the dynamic image, a parent time range TR0 for setting the first time range TR1 and the second time range TR2 (see FIG. 3). The first time range TR1 and the second time range TR2 are herein both included in the parent time range TR0.

FIG. 8 is a schematic diagram for explaining the time range setting processing (1), and shows the relationship between the parent time range TR0 and the first time range TR1 and the second time range TR2. As illustrated in FIG. 8, in parent time range setting processing (1), the parent time range TR0 for setting the first time range TR1 and the second time range TR2 (an example of setting a single second time range TR2 is shown in FIG. 8) is set in the overall time TA of the dynamic image. In this case, the first time range TR1 and the second time range TR2 are both included in the parent time range TR0, and may or may not overlap each other.

<1-3-1-3-2. Time Range Setting Processing (2)>

Assumed in the time range setting processing (2) is a case where the second time range TR2 is a single second time range TR2 when the second time range TR2 is set under a setting condition of the time range setting processing (1). That is to say, in the second time range setting processing in the time range setting processing (2), processing to set the second time range TR2 so that the second time range TR2 is equal to the overall time range of the parent time range TR0 is performed.

Figure 9:
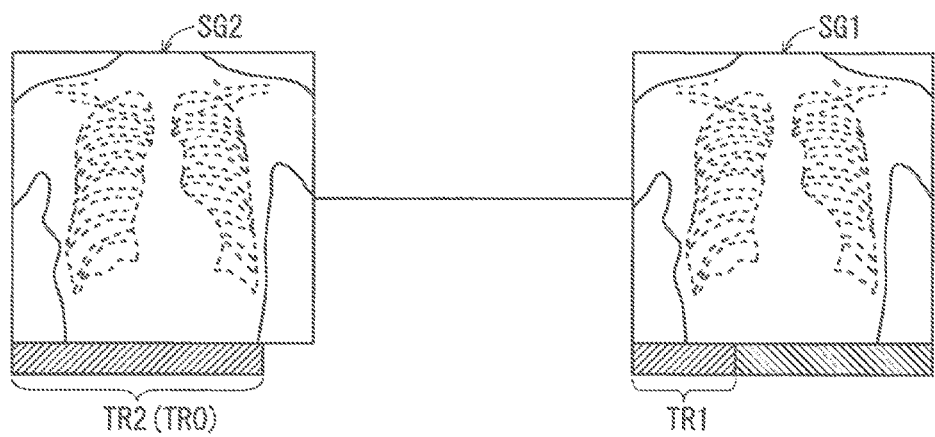
FIG. 9 is a schematic diagram for explaining the time range setting processing.

FIG. 9 is a schematic diagram for explaining the time range setting processing (2), and shows the relationship between the parent time range TR0 and the first time range TR1 and the second time range TR2. As illustrated in FIG. 9, in the second time range setting processing, processing to set the second time range TR2 so that the second time range TR2 is equal to the overall time range of the parent time range TR0 is performed. In the parent time range setting processing, the first time range TR1 is set in the parent time range TR0 (TR2).

<1-3-1-3-3. Time Range Setting Processing (3)>

In the time range setting processing (3), in addition to the setting condition of the time range setting processing (1), processing to set the first time range TR1 and the second time range TR2 so that all the time ranges of the first time range TR1 and the second time range TR2 do not overlap each other, and are continuous may be performed.

Figure 10:
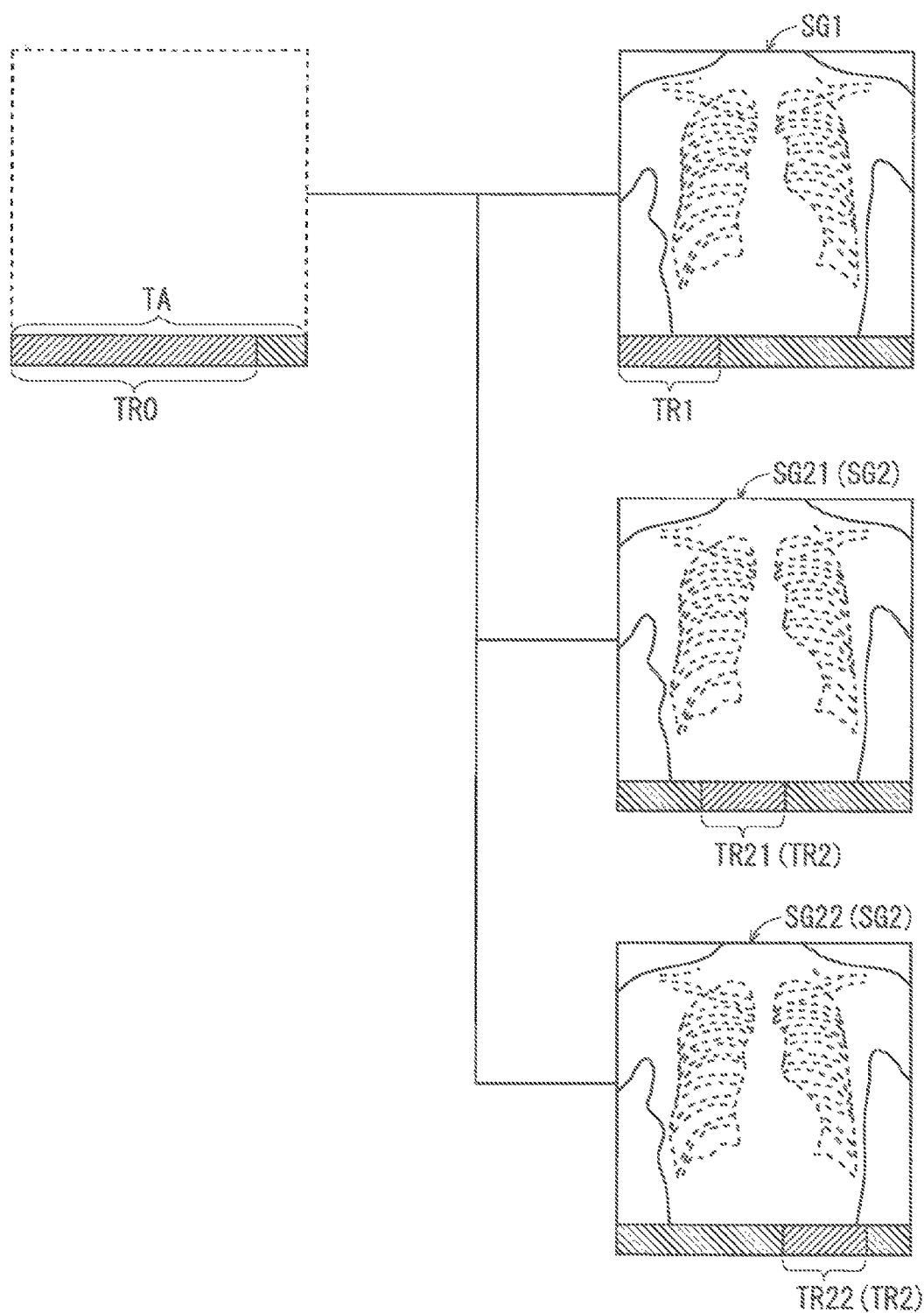
FIG. 10 is a schematic diagram for explaining the time range setting processing.

FIG. 10 is a schematic diagram for explaining the time range setting processing (3), and shows the relationship between the parent time range TR0 and the first time range TR1 and the second time range TR2. FIG. 10 illustrates a case where the second time range TR2 is composed of two second time ranges TR21 and TR22.

As illustrated in FIG. 10, in the time range setting processing (3), the first time range TR1 and the second time range TR2 are set so that the first time range TR1 and the second time range TR21 do not overlap each other, the second time range TR21 and the second time range TR22 do not overlap each other, the first time range TR1 and the second time range TR21 are continuous, and the second time range TR21 and the second time range TR22 are continuous.

<1-3-1-3-4. Time Range Setting Processing (4)>

In the time range setting processing (4), in addition to setting conditions of the time range setting processing (1) and (3), processing to set the first time range TR1 and the second time range TR2 so that a total time range of the first time range TR1 and the second time range TR2 matches the parent time range TR0 may be performed.

Figure 11:
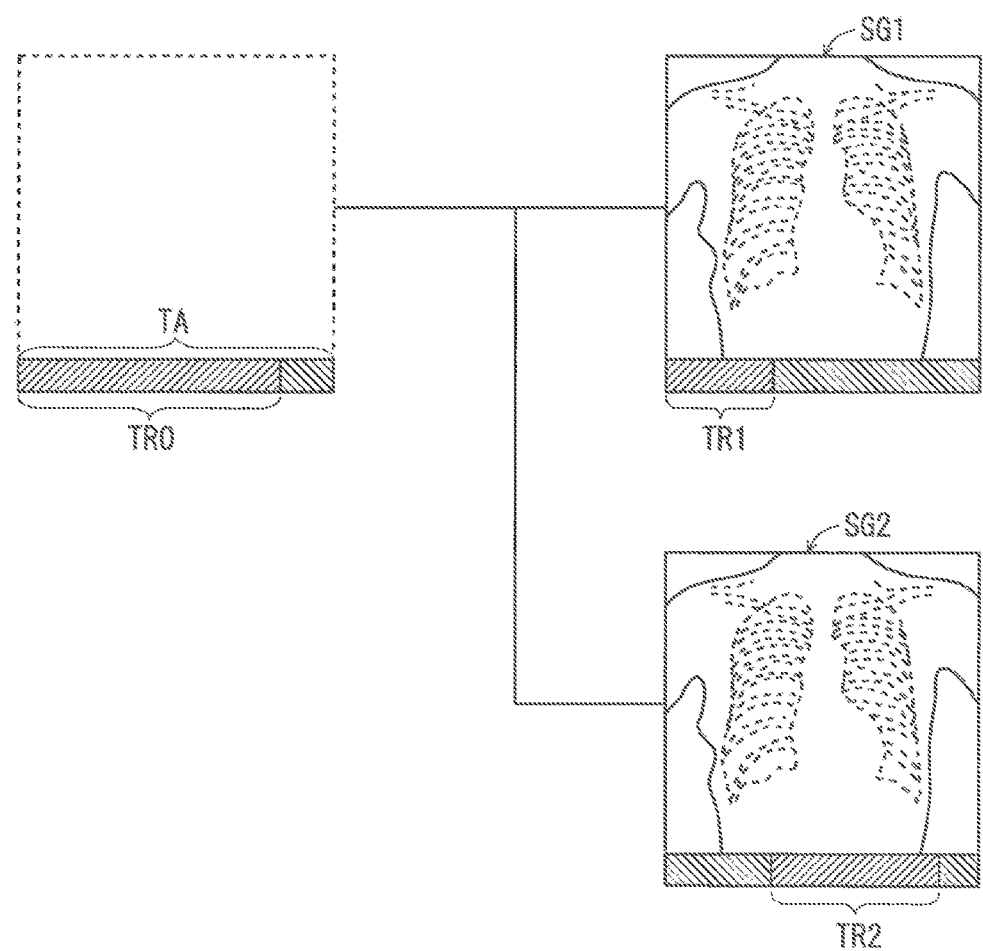
FIG. 11 is a schematic diagram for explaining the time range setting processing.
Figure 12:
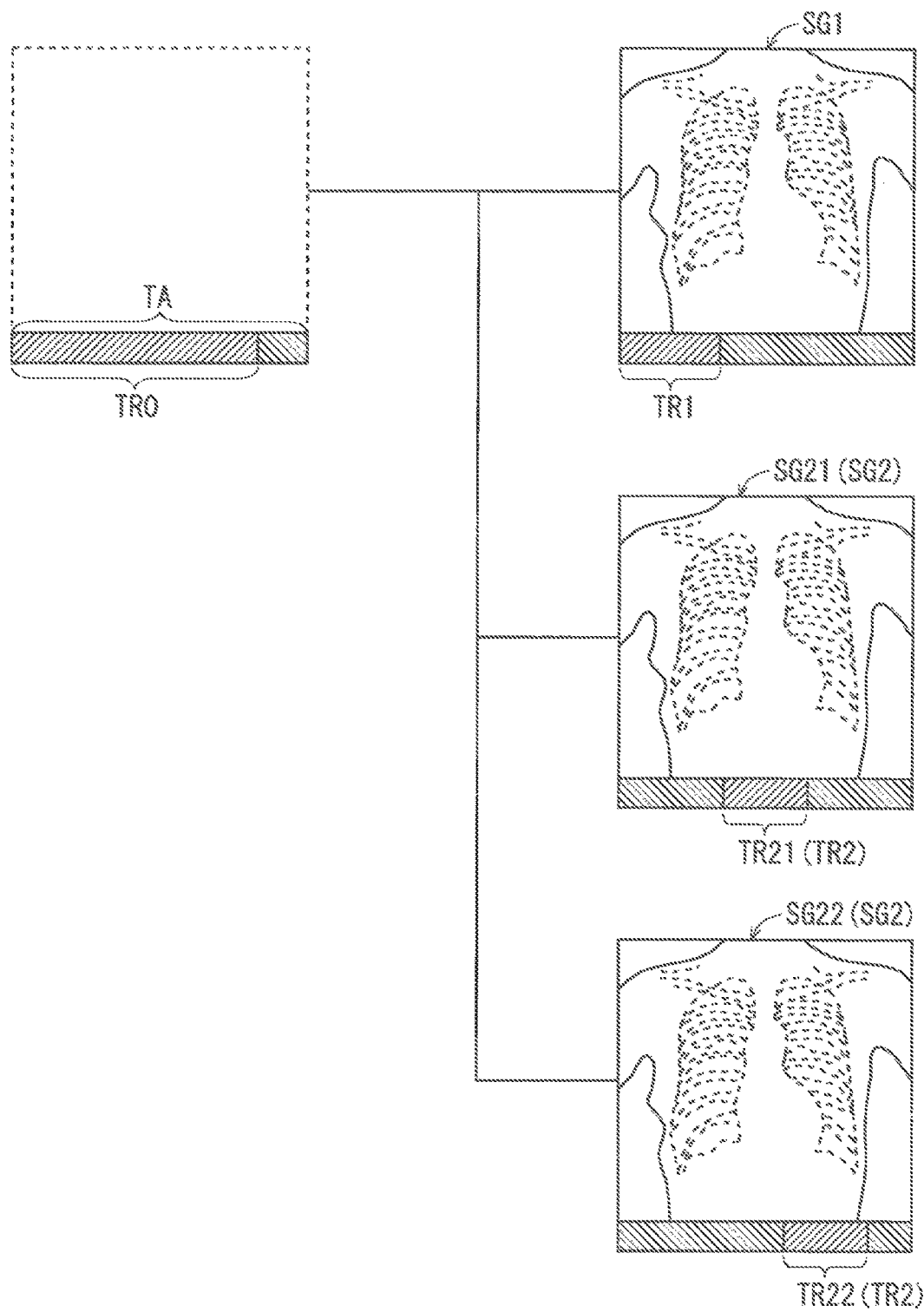
FIG. 12 is a schematic diagram for explaining the time range setting processing.

FIGS. 11 and 12 are schematic diagrams for explaining the time range setting processing (4), and show the relationship between the parent time range TR0 and the first time range TR1 and the second time range TR2. FIG. 11 illustrates a case where the second time range TR2 is a single second time range TR2, and FIG. 12 illustrates a case where the second time range TR2 is composed of the two second time ranges TR21 and TR22.

In the case of FIG. 11, in the time range setting processing (4), the first time range TR1 and the second time range TR2 are set so that the first time range TR1 and the second time range TR2 do not overlap each other and are continuous, and the total time range of the first time range TR1 and the second time range TR2 matches the parent time range TR0 (the relationship "TR0=TR1+TR2" is satisfied).

On the other hand, in the case of FIG. 12, in the time range setting processing, the first time range TR1 and the second time range TR2 are set so that the first time range TR1 and the second time range TR21 do not overlap each other and are continuous, the second time range TR21 and the second time range TR22 do not overlap each other and are continuous, and the total time range of the first time range TR1, the second time range TR21, and the second time range TR22 matches the parent time range TR0 (the relationship "TR0=TR1+TR21+TR22" is satisfied).

<1-3-1-3-5. Time Range Setting Processing (5)>

In the time range setting processing, in addition to the setting condition of the time range setting processing (1), processing to set the first time range TR1 and the second time range TR2 so that all the time ranges of the first time range TR1 and the second time range TR2 include the same number of cardiac periods PC may be performed. That is to say, the first time range TR1 and the second time range TR2 may be set so that, if the number of cardiac periods PC is represented by n (n is a positive integer) and PC is fixed, the relationship "first time range TR1=second time range TR2=n×PC" is satisfied.

Figure 13:
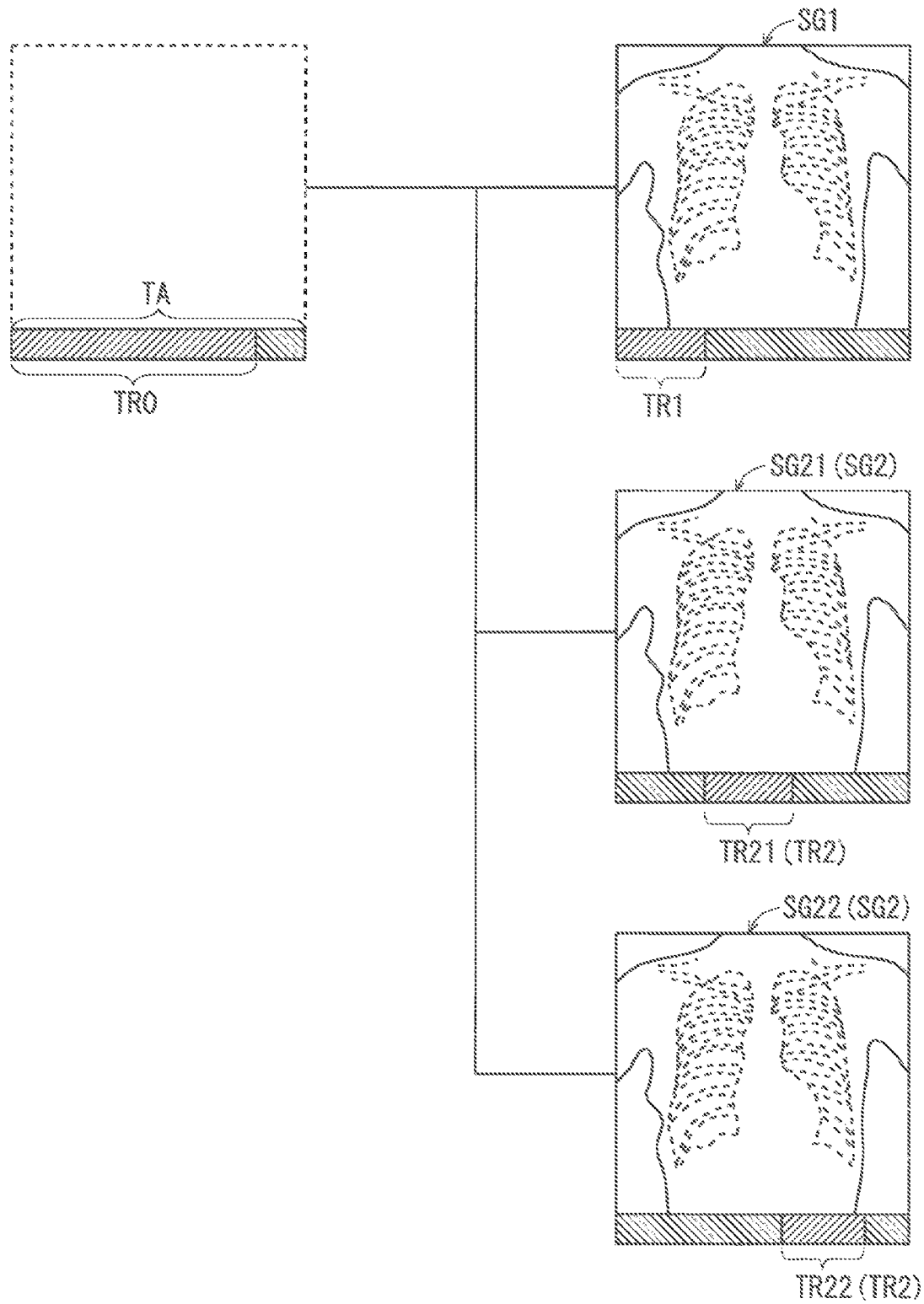
FIG. 13 is a schematic diagram for explaining the time range setting processing.

FIG. 13 is a schematic diagram for explaining the time range setting processing (5), and shows the relationship between the parent time range TR0 and the first time range TR1 and the second time range TR2. FIG. 13 illustrates a case where the second time range TR2 is composed of the two second time ranges TR21 and TR22.

As illustrated in FIG. 13, in the time range setting processing (5), the first time range TR1 and the second time range TR2 are set so that the first time range TR1, the second time range TR21, and the second time range TR22 include the same number of cardiac periods PC.

<1-3-1-3-6. Modification of Time Range Setting Unit 120>

Although the time range setting processing (1) to (5) performed by the time range setting unit 120 has been described above, the time range setting processing (1) to (5) is not limited to that described above. A modification of the time range setting unit 120 is described herein. FIG. 14 is a diagram for explaining the modification (a time range setting unit 120') of the time range setting unit 120.

As illustrated in FIG. 14, the time range setting unit 120' performs the following processing in addition to the setting condition of the time range setting processing (1). In the parent time range setting processing (a parent time range setting unit 123'), processing to set one of the first time range TR1 and the second time range TR2 as a parent time range TR0n for hierarchical display and processing to newly set the parent time range TR0n for hierarchical display as the parent time range TR0 are performed. In the first time range setting processing (a first time range setting unit 121'), processing to newly set the first time range TR1 in the parent time range TR0n for hierarchical display is displayed, and, in the second time range setting processing (a second time range setting unit 122'), processing to newly set the second time range TR2 in the parent time range TR0n for hierarchical display is performed.

Figure 15:
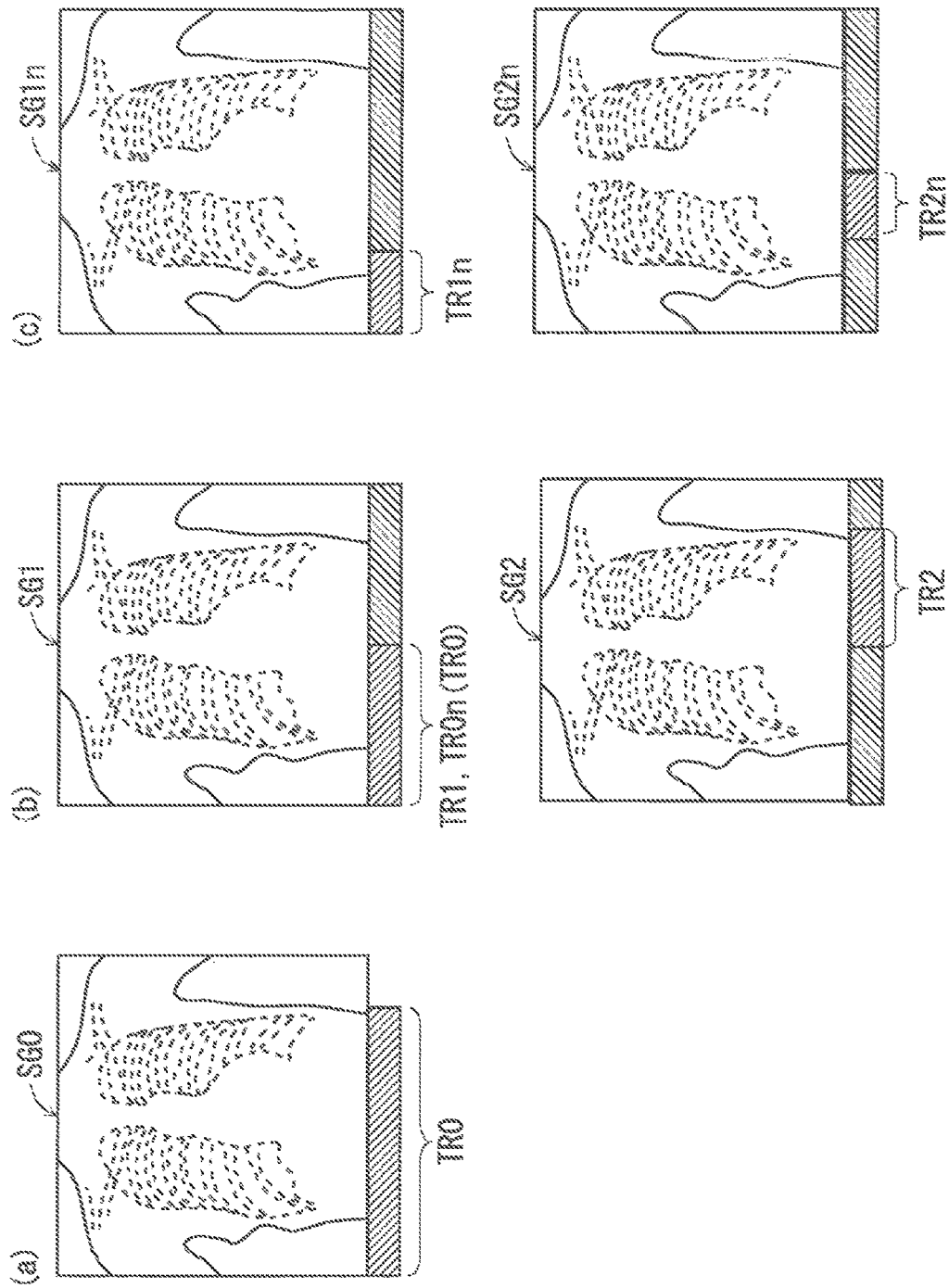
FIG. 15 is a schematic diagram for explaining the time range setting processing.

FIG. 15 is a schematic diagram for explaining the time range setting unit 120', and shows the relationship among the parent time range TR0, the first time range TR1 and the second time range TR2, and the parent time range TR0n for hierarchical display.

As illustrated in FIG. 15, after the time range setting unit 120' sets the first time range TR1 and the second time range TR2 in the parent time range TR0 illustrated in part (a) of FIG. 15 as in FIGS. 8 to 13, one of the first time range TR1 and the second time range TR2 is newly set as the parent time range TR0n for hierarchical display (see part (b) of FIG. 15). That is to say, the parent time range setting unit 123' sets, as the parent time range TR0n for hierarchical display, one of the first time range TR1 and the second time range TR2 once set, and newly sets the parent time range TR0n for hierarchical display as the parent time range TR0. Although the first time range TR1 is set as the parent time range TR0n for hierarchical display in the example of part (b) of FIG. 15, the second time range TR2 may be set as the parent time range TR0n for hierarchical display.

Then, the first time range setting unit 121' performs processing to newly set a first time range TR1n in the parent time range TR0n for hierarchical display, and the second time range setting unit 122' performs processing to newly set a second time range TR2n in the parent time range TR0n for hierarchical display (see part (c) of FIG. 15).

Although the time range setting unit 120 and the time range setting unit 120' have been described above, it is desirable to set the second time range TR2 in multiples of the cardiac period PC (time composed of one or more cardiac periods PC) as with the first time range TR1. This is because thumbnail images SG (described in detail below) can be generated in multiples of the cardiac period PC, and such thumbnail images SG are suitable for comparison. The frame images MI constituting the dynamic image, however, may not be data in multiples of the cardiac period PC, and, in this case, the cardiac periods PC leave a fraction. In this case, the first time range TR1 and the second time range TR2 are set by discarding the fraction. In contrast, the first time range TR1 and the second time range TR2 may be set so as to include the fraction to use data of the dynamic image as a whole.

<1-3-1-4. Thumbnail Generating Unit 130>

The thumbnail generating unit 130 (thumbnail generating processing) performs thumbnail generating processing to generate a first thumbnail image SG1 that is a still image obtained by performing statistical processing on a dynamic image in the first time range TR1 using frame images in the first time range TR1 and a second thumbnail image SG2 that is a still image obtained by performing the statistical processing on a dynamic image in the second time range TR2 using frame images in the second time range TR2 (see FIG. 3).

That is to say, as illustrated in FIGS. 7 to 13 and 15, the thumbnail generating unit 130 generates the thumbnail image SG1 (SG1n) using frame images MI in the first time range TR1 (TR1n) set by the first time range setting unit 121 (121'), and generates the thumbnail image SG2 (SG2n) using frame images MI in the second time range TR2 (TR2n) set by the second time range setting unit 122 (122').

In a case where the overall time TA of the dynamic image is a target for analysis, by generating the first thumbnail image SG1 using one particular period of the dynamic image as the first time range TR1, and generating the second thumbnail image SG2 using the overall time TA as the second time range TR2, a state of the one particular period can be displayed so as to be compared with the dynamic image as a whole for check. Even if the particular period includes a plurality of cardiac periods PC, the first time range TR1 is set in multiples of the cardiac period PC to generate the first thumbnail image SG1, and thus an appropriate thumbnail image for comparison relative to an overall size of the dynamic image can be generated.

The thumbnail generating unit 130 (thumbnail generating processing) herein includes: a statistical value calculating unit 141 (statistical value calculating processing) to calculate, with respect to the first time range TR1 or the second time range TR2, a pixel statistical value SM (first pixel statistical value SM1 and second pixel statistical value SM2) for each corresponding pixel in a time direction, i.e., for each corresponding pixel among frame images; and a pixel value determining unit 142 (pixel value determining processing) to determine a pixel value for the first thumbnail image SG1 or the second thumbnail image SG2 based on the pixel statistical value SM (see FIG. 3).

The first pixel statistical value SM1 in the first time range TR1 and the second pixel statistical value SM2 in the second time range TR2 calculated through the statistical value calculating processing are hereinafter simply referred to as a "pixel statistical value SM1" and a "pixel statistical value SM2", respectively.

The pixel statistical value SM (pixel statistical values SM1 and SM2) herein refers to any of a total value, an average value, a maximum value, a minimum value, a median value, and the like of pixel density calculated with respect to the first time range TR1 or the second time range TR2 using a difference value (pixel density) of a corresponding pixel between frame images MI close to each other in terms of time in the first time range TR1 or the second time range TR2. As described above, the pixel statistical value SM indicates pixel density, and thus, in a case where a maximum value of the difference value is used, for example, if the maximum value is small, a low pixel density is reflected. Thus, blood flow can be presumed to be poor. As a result, the lack of blood flow and the difference in roughness per cardiac period PC can be determined through comparison.

In this case, in the statistical value calculating processing (statistical value calculating unit 141), it is preferable to perform processing to normalize the pixel statistical values SM1 and SM2 by the number of cardiac periods PC included in the time ranges with respect to which the pixel statistical values SM1 and SM2 have been calculated.

A specific example of normalization by the number of cardiac periods PC is as follows; in a case where the pixel statistical values SM1 and SM2 are total values, if the number of cardiac periods PC in the first time range TR1 with respect to which the pixel statistical value SM1 has been calculated is 3 (TR1=3×PC) and the number of cardiac periods PC in the second time range TR2 with respect to which the pixel statistical value SM2 has been calculated is 10 (TR2=10×PC), the pixel statistical value SM1 (total value of the difference value) is divided by 3, and the pixel statistical value SM2 (total value of the difference value) is divided by 10.

By using the difference value (also referred to as a blood flow analysis value) of a corresponding pixel between the frame images MI (MI') close to each other in terms of time to calculate the pixel statistical value SM, a value of a change in blood flow density can be visualized, and the speed and the direction of blood flow can be viewed. That is to say, a delay in flow in a blood vessel relative to pulsation of the heart or a delay in flow in a blood vessel relative to a surrounding region suggests the possibility that the blood vessel has a thrombus, which is one of matters to be checked the most in the blood flow dynamic image. The direction of blood flow is an important aspect to make a distinction from various types of noise. Therefore, a value reflecting the delay in flow in the blood vessel and the direction of blood flow may be used as the pixel statistical value SM.

For example, the delay in flow in the blood vessel and the direction of blood flow can be checked by using a spatial correlation value of the difference value as the pixel statistical value SM that facilitates viewing of the delay in flow in the blood vessel and the direction of blood flow. That is to say, by calculating a degree of correlation with difference values in a surrounding region as the spatial correlation value, the delay in speed and direction of blood flow can be presumed.

Specifically, a state indicating the "delay" refers to a state in which the spatial correlation value between a blood flow value (difference value) at a target pixel and blood flow values at pixels spatially surrounding the target pixel is small. That is to say, if there is blood flow at the target pixel, but there is no blood flow at the majority of surrounding pixels, the possibility of delay at the target pixel is assumed to be high.

As for display on the thumbnail image SG relating to the delay and the direction, blood flow values are displayed in different colors <R, G, and B> depending on the phase of blood flow and photographing time. For example, pixel values are generated such that pixel statistical values SM corresponding to a main vascular phase and a peripheral vascular phase, which are arterial phases, are respectively reflected in an R-value and a G-value, and a pixel statistical value SM corresponding to a venous phase is reflected in a B-value.

The pixel statistical value SM may be calculated using a pixel value in a part of the first time range TR1 and the second time range TR2 that are targets of the first thumbnail image SG1 and the second thumbnail SG2. That is to say, a time range is selected at a timing at which blood flow delayed relative to normal blood flow can be visualized to calculate the pixel statistical value SM to thereby generate a thumbnail image SG reflecting the delay.

The part of the time range is herein preferably determined from phase information of blood flow (dynamics). That is to say, a method of calculating a blood flow analysis value of only the arterial phase (blood flow phase) as the pixel statistical value SM, a method of calculating a blood flow analysis value of a phase other than a maximum inhalation phase (respiratory phase) as the pixel statistical value SM, a method of calculating a blood flow analysis value of a phase suitable for visualization of delayed blood flow as the pixel statistical value SM, and the like can be used. As described above, by determining the pixel statistical value SM from the phase of dynamics and generating the thumbnail image SG, the user can determine a more appropriate timing from the thumbnail image.

FIG. 16 is a diagram for explaining the thumbnail generating processing in a case where the pixel statistical value SM is the maximum value of pixel density. Part (a) of FIG. 16 is a diagram for schematically explaining the relationship between the frame images MI in the first time range TR1 (or second time range TR2) set in the time range setting processing and the cardiac period PC. The horizontal and vertical axes respectively represent photographing time and the width of the heart acquired in the cardiac period acquiring processing or an electrical signal detected from the electrocardiograph 4. Part (b) of FIG. 16 illustrates the thumbnail image SG1 (SG2) generated using the maximum value of the difference value between the frame images MI in the time range TR1 (TR2) of part (a) of FIG. 16.

In the example of part (a) of FIG. 16, the time range TR1 (TR2) is set so as to include one cardiac period PC, the number of frame images MI in the time range TR1 (TR2) is seven, and the number of time differences $\Delta t1$ to $\Delta t6$ is six, but this is just an example, and these values are actually set in accordance with a frame rate in moving image photography.

As shown in part (a) of FIG. 16, the difference between the frame images MI in the time range TR1 (TR2) is first obtained in order of photographing time, and difference values d1 to d6 corresponding to the respective time differences $\Delta t1$ to $\Delta t6$ are then obtained to obtain the difference values for one cardiac period PC. A maximum value of the difference values dl to d6 is calculated as the pixel statistical value SM in the statistical value calculating processing, and a pixel value for the first thumbnail image SG1 (or second thumbnail image SG2) is determined based on the pixel statistical value SM in the pixel value determining processing. As a result, a single first thumbnail image SG1 (or second thumbnail image SG2) can be obtained as illustrated in part (b) of FIG. 16.

That is to say, each of the difference values dl to d6 corresponds to blood flow in the lung field. For example, at the peak of the heart rate (see a point Rp of part (a) of FIG. 16), blood flow is concentrated in the vicinity of the heart, and thus a density difference increases and a difference value increases on the frame image in the vicinity of the heart (see, for example, a region dr of part (b) of FIG. 16). In contrast, at time distant from the peak of the heart rate (see, for example, a point Up of part (a) of FIG. 16), blood flow is concentrated in a region distant from the heart, and thus a density difference increases and a difference value increases on the frame image in the region distant from the heart (see, for example, a region du of part (b) of FIG. 16).

As described above, a large difference value (density difference) moves (spatially changes) on the frame images with photographing time between the frame images MI (temporal change). The difference between the frame images MI corresponding to one cardiac period PC1 is obtained to calculate a maximum value of each difference value as the pixel statistical value SM, a single thumbnail image SG is then generated based on the pixel statistical value SM, and, as a result, the whole picture of circulation of blood flow in the entire lung field region can be seen. Thus, even movement of blood flow in the lung field can be understood, for example, by finding a part of the lung field region in which there is no blood flow if the test subject M is not a healthy individual.

Although the pixel statistical value SM is treated as the maximum value of pixel density in the example of FIG. 16, the pixel statistical value SM may obviously be any of the average value, the maximum value, the minimum value, the median value, and the like of pixel density.

In place of the method for calculating the pixel statistical value SM described with use of FIG. 16, a method of extracting only a desired signal using a low-pass filter and a high-pass filter to calculate the pixel statistical value SM may be used.

<1-3-1-5. Display Unit 34 and Operation Unit 33>

The display unit 34 displays the first thumbnail image SG1 and the second thumbnail image SG2 so that the first thumbnail image SG1 and the second thumbnail image SG2 can visually be compared with each other. The operation unit 33 receives setting information set by the user. This means that the user can input the setting information, which is described below, through the operation unit 33.

The display unit 34 can display the dynamic image based on the frame images MI (including time information) acquired by the dynamic image acquiring unit 110.

The display unit 34 can further receive information on the first time range TR1 and the second time range TR2 as information for the first thumbnail image SG1 and the second thumbnail image SG2 received from the thumbnail generating unit 130 to play back and display the dynamic images in the first time range TR1 and the second time range TR2.

Methods for displaying the first thumbnail image SG1 and the second thumbnail image SG2 displayed by the display unit 34 are each described below.

<1-3-1-5-1. Thumbnail Display Method (1)>

In a thumbnail display method (1), the display unit 34 performs processing to play back a dynamic image corresponding to a thumbnail image for moving image comparison based on the setting information inputted through the operation unit 33. The setting information herein refers to information for setting one of the first thumbnail image SG1 and the second thumbnail image SG2 as the thumbnail image for moving image comparison.

Figure 17:
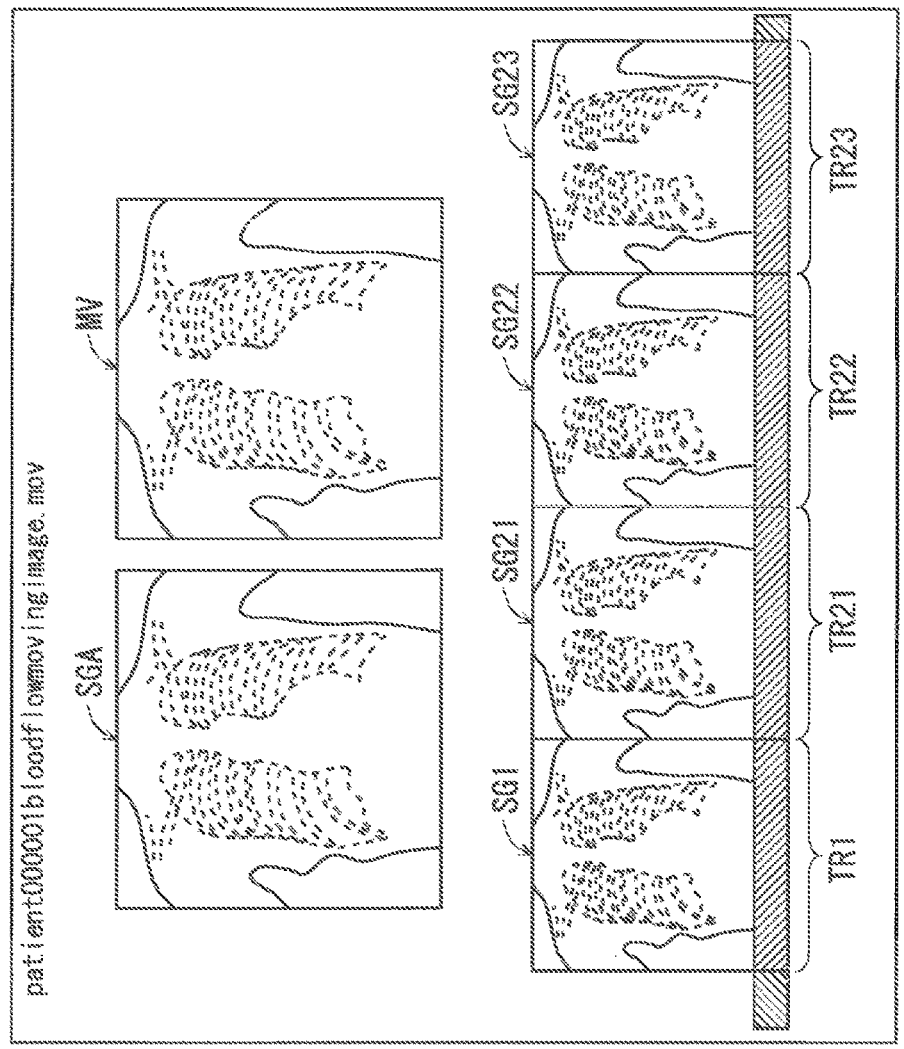
FIG. 17 is a schematic diagram for explaining thumbnail display processing.

FIG. 17 is a schematic diagram illustrating the thumbnail display method (1). Part (a) of FIG. 17 shows a selection screen (an explorer) EP for selecting a target dynamic image, and part (b) of FIG. 17 illustrates a thumbnail display screen corresponding to a dynamic image having been selected from the selection screen EP by the user. FIG. 17 illustrates a case where the second time range TR2 is composed of a plurality of second time ranges TR2, which are represented by three second time ranges TR21, TR22, and TR23.

As illustrated in FIG. 17, if the user selects "patient000001bloodflowmovingimage.mov" from the selection screen EP shown in part (a) of FIG. 17, an overall thumbnail image SGA in the overall time TA, the first thumbnail image SG1 in the first time range TR1, and the second thumbnail image SG2 (SG21 to SG23) in the second time range TR2 (TR21 to TR23) of a dynamic image corresponding to "patient000001bloodflowmovingimage.mov" are displayed as illustrated in part (b) of FIG. 17. The thumbnail image SGA in the overall time TA is generated by the thumbnail generating unit 130 based on the frame images MI acquired by the dynamic image acquiring unit 110.

As described above, in display for diagnosis made by the user, a blood flow analysis dynamic image for each patient is displayed by using the overall thumbnail image SGA, the first thumbnail image SG1, and the second thumbnail image SG2 as a cover. Assume that the first thumbnail image SG1 and the second thumbnail image SG2 displayed in the thumbnail display method (1) have been generated through division into the cardiac periods PC.

The user makes rough diagnosis on the feature of blood flow using the overall thumbnail image SGA in the overall time range TA, and then selects a desired thumbnail image SG from the displayed thumbnail images SG1 and SG21 to SG23. That is to say, in a case where, for example, the user determines that blood flow in a particular region is thinner than that in a surrounding region from the overall thumbnail image SGA, but is not sure whether the particular region is a region with a blood flow abnormality or photographing noise, the user can select, through the operation unit 33, a thumbnail image SG more clearly reflecting the abnormality to make more detailed diagnosis. A dynamic image corresponding to the selected thumbnail image SG is played back by a playback display unit MV.

It is desirable to attach a playback time of a dynamic image to each of the first thumbnail image SG1 and the second thumbnail SG2 generated in multiples of the cardiac period PC. For example, the speed of pulse is higher in a cardiac period PC in which arrhythmia occurs than in the other cardiac periods PC, and thus the cardiac period PC in which arrhythmia occurs is shorter than the other cardiac periods PC. This is reflected in a shorter playback time of the dynamic image corresponding to the thumbnail image SG, so that arrhythmia can efficiently be diagnosed. In addition, in a case where the appearance varies among cardiac periods PC due to photographing noise and the like, a cardiac period PC more suitable for diagnosis or a cardiac period PC not suitable for diagnosis can be understood through comparison between thumbnail images SG, and thus a moving image as a target for playback can efficiently be selected.

A dynamic image corresponding to the first thumbnail image SG1 or the second thumbnail image SG2 designated by the user may or may not be played back with respect to the first time range TR1 or the second time range TR2 set in the time range setting processing. That is to say, the dynamic image may be played back and displayed by including time around the first time range TR1 or the second time range TR2 set in the time range setting processing. As a result, the dynamic image can be played back and displayed with respect to a range adjusted to be greater or smaller than the first time range TR1 or the second time range TR2 set in the time range setting processing in consideration of a certain phase unit, such as a timing of output or input of blood flow from or to the heart.

Furthermore, the number of cardiac periods PC included in the first time range TR1 in the first thumbnail image SG1 or the second time range TR2 in the second thumbnail image SG2 may also be displayed. In addition, with respect to the first thumbnail image SG1 or the second thumbnail image SG2, the first time range TR1 in the first thumbnail image SG1 or the second time range TR2 in the second thumbnail image SG2, the overall time TA of the dynamic image, and the parent time range TR0 may also be displayed.

Furthermore, as described above, in a case where the first time range TR1 or the second time range TR2 is set by discarding the fraction as a result of the cardiac periods PC leaving the fraction, the fact that the fractional time has been excluded may be displayed to clearly show the state of the time range included in the first time range TR1 or the second time range TR2.

As described above, in the thumbnail display method (1), the display unit 34 performs processing to play back the dynamic image corresponding to the thumbnail image for moving image comparison based on the setting information (information indicating the thumbnail image for moving image comparison) inputted through the operation unit 33. This allows the user to perform operation to compare the thumbnail images (still images) SG and operation to view the dynamic image in parallel to each other. As a result, dynamic diagnosis can properly and efficiently be made.

<1-3-1-5-2. Thumbnail Display Method (2)>

In a thumbnail display method (2), processing to generate the thumbnail image SG in a predetermined time range indicated by the setting information inputted through the operation unit 33 by performing statistical processing using frame images in the predetermined time range is performed in the thumbnail generating processing, and the display unit 34 performs processing to display the thumbnail image SG in the predetermined time range. The setting information herein refers to information for setting the predetermined time range.

In a case where the predetermined time range is the parent time range TR0, processing to set the parent time range TR0 based on the setting information inputted through the operation unit 33 is performed in the parent time range setting processing, the time range setting unit 120 and the thumbnail generating unit 130 operate, and the display unit 34 displays the first thumbnail image SG1 in the first time range TR1 and the second thumbnail image SG2 in the second time range TR2 divided from the parent time range TR0.

Figure 18:
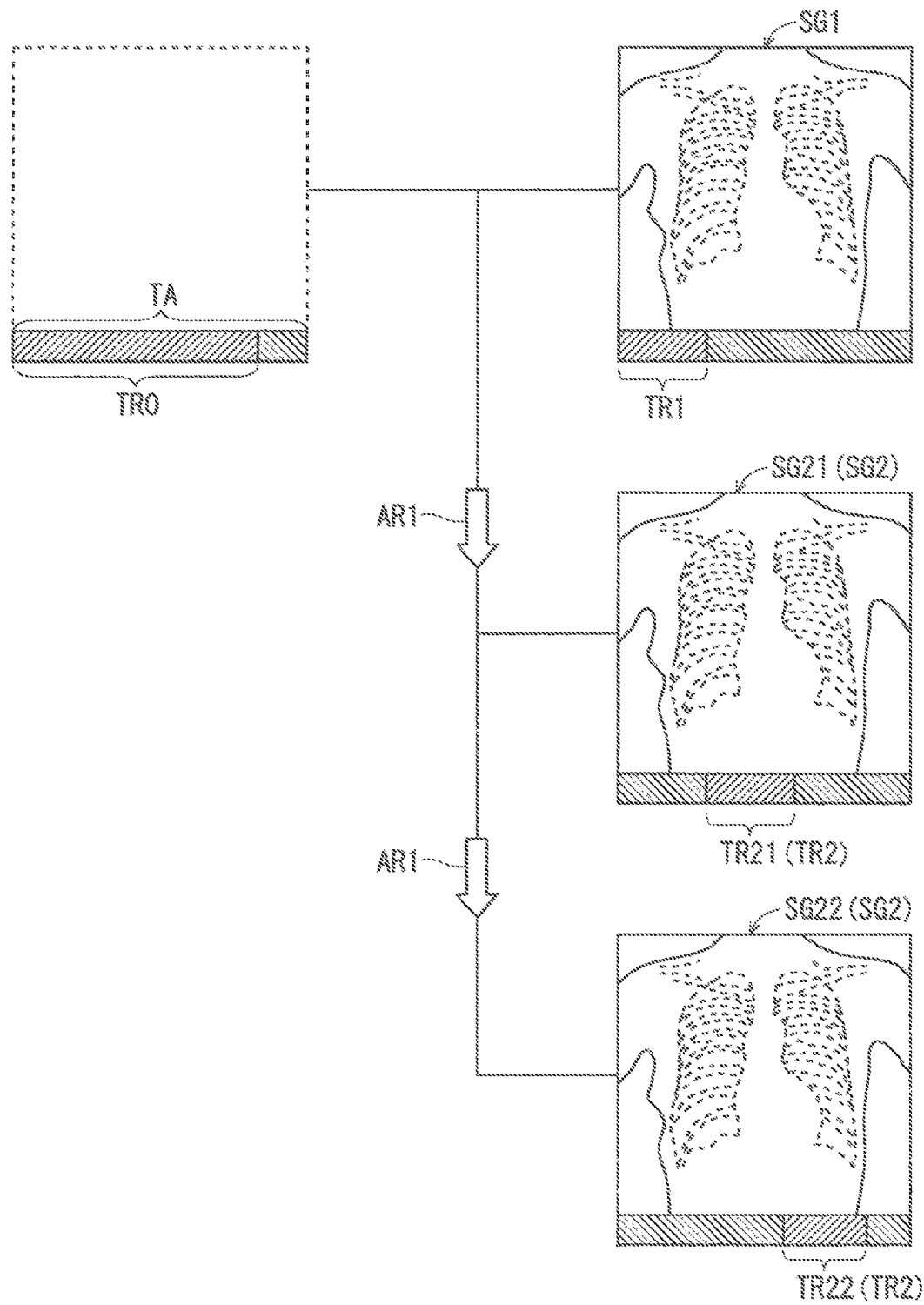
FIG. 18 is a schematic diagram for explaining the thumbnail display processing.

FIG. 18 is a schematic diagram illustrating the thumbnail display method (2) in a case where the predetermined time range is the parent time range TR0. Although the overall thumbnail image SGA in the overall time TA of the dynamic image and the playback display unit MV for playing back the dynamic image corresponding to the selected thumbnail image SG as illustrated in FIG. 17 are not illustrated in FIG. 18, similar functions may be provided in FIG. 18.

When the user selects the parent time range TR0 inputted through the operation unit 33 as a target for analysis, a user interface (UI) for parallel development display of the display unit 34 is activated, and the display unit 34 displays the first thumbnail image SG1 and the second thumbnail image SG2 (SG21 and SG22) suitable for analysis of the dynamic image in parallel to each other in accordance with the instruction from the user as illustrated in FIG. 18. In FIG. 18, the thumbnail images are developed by the UI as shown by arrows AR1.

As described above, in the thumbnail display method (2), the thumbnail generating processing further includes processing to generate the thumbnail image in the predetermined time range indicated by the setting information inputted through an operation unit by performing the statistical processing using the frame images in the predetermined time range, and a display unit performs processing to display the thumbnail image in the predetermined time range. As a result, when the user inputs the predetermined time range through the operation unit, the thumbnail image in the predetermined time range is displayed.

In a case where the predetermined time range is the parent time range TR0, processing to set the parent time range TR0 based on the setting information inputted through the operation unit 33 is performed in the parent time range setting processing. That is to say, when the user inputs the parent time range TR0 as the target for analysis through the operation unit 33, the thumbnail images SG obtained by dividing data of the dynamic image in the target for analysis are displayed. As a result, the parent time range TR0 desired by the user is automatically divided.

<1-3-1-5-3. Thumbnail Display Method (3)>

In a thumbnail display method (3), the display unit 34 performs processing to hide the first thumbnail image SG1 or the second thumbnail image SG2 in a time range included in a hidden time range based on the setting information inputted through the operation unit 33. The setting information herein refers to information for setting the parent time range TR0 and information for setting the hidden time range.

FIG. 19 is a schematic diagram illustrating the thumbnail display method (3). Although the overall thumbnail image SGA in the overall time TA of the dynamic image and the playback display unit MV for playing back the dynamic image corresponding to the selected thumbnail image SG as illustrated in FIG. 17 are not illustrated in FIG. 19, similar functions may be provided in FIG. 19.

When the user selects the hidden time range inputted through the operation unit 33, the display unit 34 hides the thumbnail image SG in the hidden time range in accordance with the instruction from the user as illustrated in FIG. 19. The hidden time range in FIG. 19 corresponds to the second time range TR2 (TR21 and TR22), and the second thumbnail image SG2 (SG21 and SG22) is hidden by the UI as shown by arrows AR2.

As described above, in the thumbnail display method (3), the display unit 34 performs processing to hide the first thumbnail image SG1 or the second thumbnail image SG2 in the time range included in the hidden time range based on the setting information inputted through the operation unit 33. For example, in a case where there are a plurality of first thumbnail images SG1 and second thumbnail images SG2 to be compared with each other for analysis, the user can designate a thumbnail image SG not required to be displayed to hide the thumbnail image SG. As a result, only the thumbnail image SG to be focused on can be displayed. The display unit 34 can thus effectively use a space on the display.

<1-3-1-5-4. Thumbnail Display Method (4)>

In a thumbnail display method (4), processing to generate a thumbnail image SGT in an aggregate time range indicated by the setting information inputted through the operation unit 33 by performing the statistical processing using frame images in the aggregate time range is further performed in the thumbnail generating processing, and the display unit 34 performs processing to hide a predetermined number of thumbnail images SG in time ranges included in the aggregate time range indicated by the setting information inputted through the operation unit 33 and processing to aggregate the predetermined number of thumbnail images SG into a single thumbnail image SGT for display. The setting information herein refers to information for setting the parent time range TR0 and information for setting a predetermined number (two or more) of time ranges of the first time range TR1 and the second time range TR2 as the aggregate time range.

Figure 21:
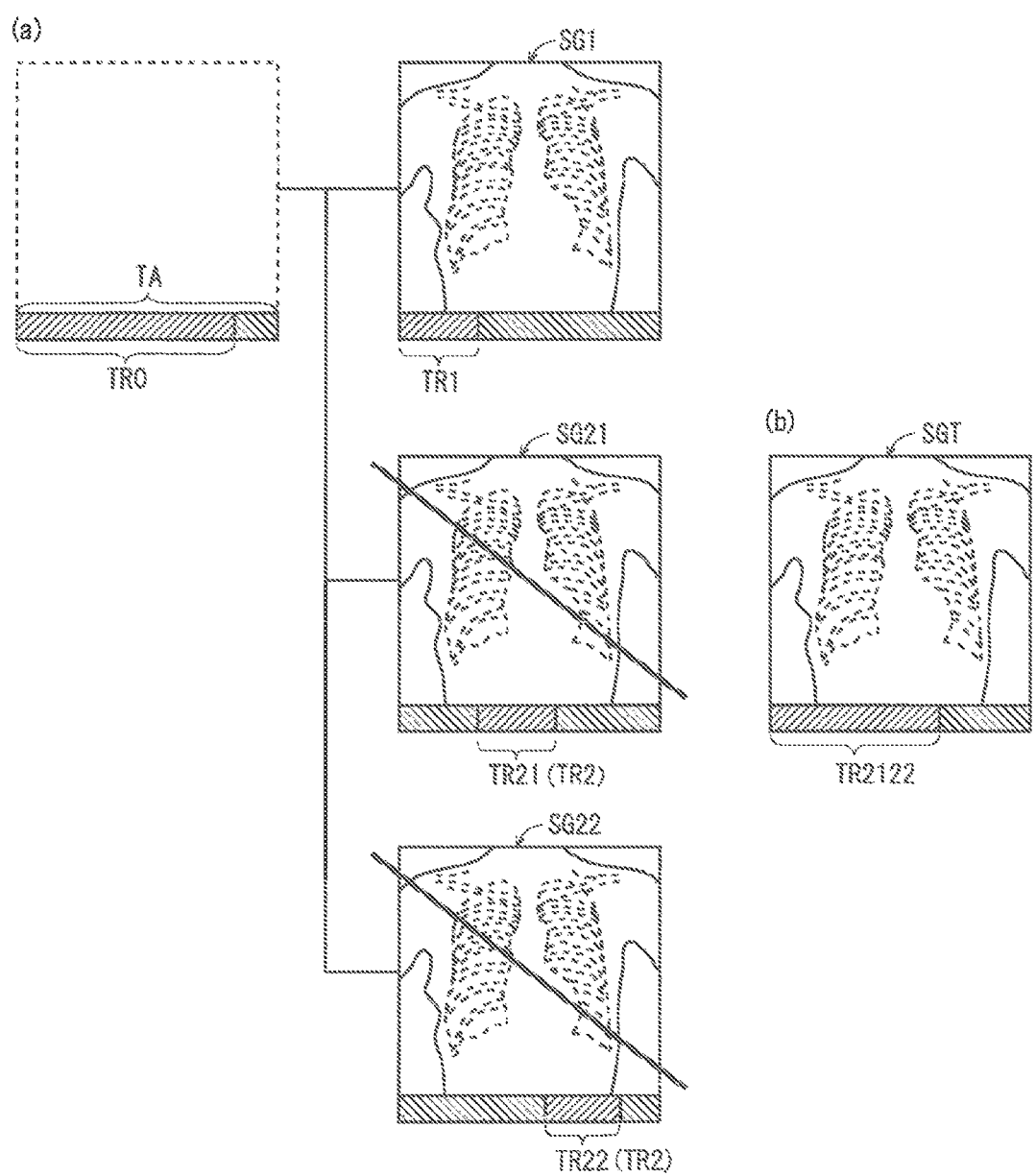
FIG. 21 is a schematic diagram for explaining the thumbnail display processing.

FIGS. 20 and 21 are schematic diagrams illustrating the thumbnail display method (4). As for the time ranges, assume that the relationship "TR0=TR1+TR2" is satisfied in the case of FIG. 20, and the relationship "TR2122=TR21+TR22" is satisfied in the case of FIG. 21.

In the case of FIG. 20, when the user designates TR0 as the aggregate time range inputted through the operation unit 33, the display unit 34 hides the first thumbnail image SG1 in the first time range TR1 included in the aggregate time range and the second thumbnail image SG2 in the second time range TR2 included in the aggregate time range in accordance with the instruction from the user, and aggregates the two thumbnail images, namely, the first thumbnail image SG1 and the second thumbnail SG2, into a single integrated thumbnail image SGT corresponding to the parent time range TR0 for display as shown by an arrow AR3.

On the other hand, as illustrated in part (a) of FIG. 21, when the user designates TR2122 as the aggregate time range inputted through the operation unit 33, the display unit 34 hides the second thumbnail image SG21 in the second time range TR21 included in the aggregate time range and the second thumbnail image SG22 in the second time range TR22 included in the aggregate time range in accordance with the instruction from the user. As illustrated in part (b) of FIG. 21, the display unit 34 then aggregates the two thumbnail images, namely, the second thumbnail images SG21 and SG22, into a single integrated thumbnail image SGT for display.

As described above, in the thumbnail display method (4), processing to generate the thumbnail image SGT in the aggregate time range indicated by the setting information inputted through the operation unit 33 by performing the statistical processing using the frame images in the aggregate time range is further performed in the thumbnail generating processing, and the display unit 34 performs processing to hide the predetermined number of thumbnail images SG in the time ranges included in the aggregate time range and processing to display the thumbnail image SGT in the aggregate time range. That is to say, in a case where there are a plurality of thumbnail images SG to be compared with each other for analysis, time ranges determined to be equivalent to each other through comparison can be integrated into a time range for a single thumbnail image SGT. This can reduce the number of thumbnail images SG not required to be compared. The display unit 34 can thus effectively use the space on the display.

<1-4. Basic Operation of Image Processing Apparatus 3>

Figure 22:
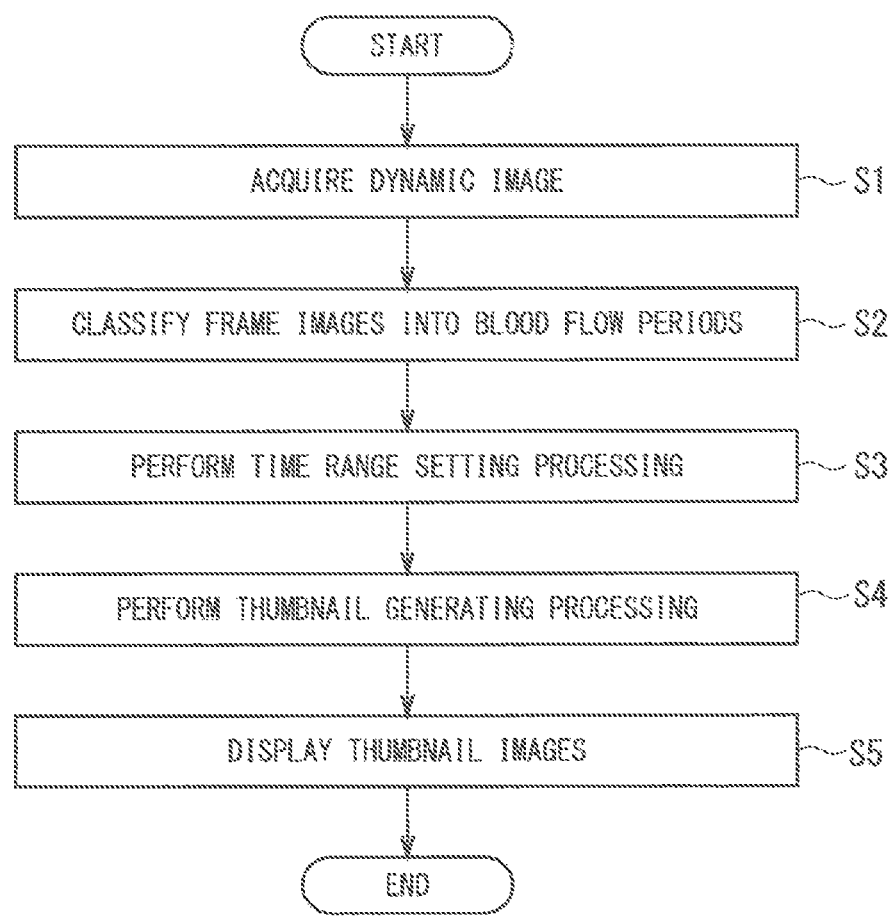
FIG. 22 is a flowchart for explaining a basic operation of the image processing apparatus 3 achieved in Embodiment 1.

FIG. 22 is a flowchart for explaining a basic operation achieved by the image processing apparatus 3 according to the present embodiment. Since an individual function of each unit has already been described (see FIG. 3), only an overall flow is described herein.

As shown in FIG. 22, in Step S1, the dynamic image acquiring unit 110 of the control unit 31 first acquires the dynamic image (frame images MI) photographed by the reading control device 14 of the photographing apparatus 1 through the photographing control apparatus 2 (see FIGS. 3 and 4).

In Step S2, the period classifying unit 115 classifies the frame images MI into the cardiac periods PC based on the cardiac periods PC in the test subject M (body) synchronized with photographing time at which the frame images MI acquired in Step S1 have been photographed to obtain the frame images MI' (see FIG. 3).

In Step S3, the time range setting unit 120 performs the time range setting processing including the first time range setting processing to set the first time range TR1 in the overall time TA of the dynamic image acquired in Step S1 in multiples of the cardiac period PC and the second time range setting processing to set the second time range TR2 in the overall time TA of the dynamic image acquired in Step S1 (see FIGS. 7 to 13). In a case where the first time range TR1 and the second time range TR2 are set in multiples of the cardiac period PC, the first time range TR1 and the second time range TR2 can easily be set using the frame images MI' obtained through classification into the cardiac periods in Step S2.

In Step S4, the thumbnail generating unit 130 (thumbnail generating processing) generates the first thumbnail image SG1, which is the still image obtained by performing the statistical processing on the dynamic image in the first time range TR1 set in Step S3, using the frame images MI in the first time range TR1, and generates the second thumbnail image SG2, which is the still image obtained by performing the statistical processing on the dynamic image in the second time range TR2 set in Step S3, using the frame images MI in the second time range TR2 (see FIGS. 3 and 16).

Finally, in Step S5, the thumbnail generating unit 130 outputs the first thumbnail image SG1 and the second thumbnail image SG2 generated in Step S4 to the display unit 34 (see FIG. 3), and the flowchart of this operation ends. The first thumbnail image SG1 and the second thumbnail image SG2 may be output not only to the display unit 34 but also to the storage unit 32 (see FIG. 1). The display unit 34 then displays the first thumbnail image SG1 and the second thumbnail image SG2 so that the first thumbnail image SG1 and the second thumbnail image SG2 can visually be compared with each other, for example, by displaying the first thumbnail image SG1 and the second thumbnail image SG2 in parallel to each other (see FIGS. 17 to 21).

As described above, the image processing apparatus 3 according to Embodiment 1 includes: the thumbnail generating unit 130 that performs the thumbnail generating processing to generate the first thumbnail image SG1, which is the still image obtained by performing the statistical processing on the dynamic image in the first time range TR1 set in the overall time of the dynamic image in multiples of the dynamic period (including one or more dynamic periods), using the frame images in the first time range TR1, and generate the second thumbnail image SG2, which is the still image obtained by performing the statistical processing on the dynamic image in the second time range TR2 set in the overall time of the dynamic image, using the frame images in the second time range TR2; and the display unit 34 that displays the first thumbnail image SG1 and the second thumbnail image SG2 so that the first thumbnail image SG1 and the second thumbnail image SG2 can visually be compared with each other. That is to say, since the first thumbnail image SG1 and the second thumbnail image SG2, which show the dynamic images as still images, are displayed so as to be visually compared with each other, the user can understand the feature into which the dynamic images in the first time range TR1 and the second time range TR2 are aggregated at a glance by viewing the first thumbnail image SG1 and the second thumbnail image SG2 without viewing the dynamic image as a whole. As a result, the difference per first time range TR1 and second time range TR2 in the dynamic image can properly and efficiently be seen. This allows the user to immediately determine and select the desired time range based on the difference per first time range TR1 and second time range TR2, leading to improvement in efficiency of diagnosis. For the above-mentioned reasons, dynamic diagnosis can properly and efficiently be made.

By performing processing to set the second time range TR2 in multiples of the cardiac period PC (in multiples of the dynamic period) in the second time range setting processing, the first time range TR1 and the second time range TR2 are both set in multiples of the cardiac period PC. The first thumbnail image SG1 and the second thumbnail image SG2 are thus generated in multiples of the cardiac period PC. As a result, the time ranges can be adjusted in multiples of the cardiac period PC, and thus the difference between them can properly be compared with each other.

In the time range setting processing (1), the parent time range setting processing to set, in the overall time TA of the dynamic image, the parent time range TR0 for setting the first time range TR1 and the second time range TR2 is performed, and the first time range TR1 and the second time range TR2 are both included in the parent time range TR0. That is to say, by setting the parent time range TR0 as the target for analysis, the first time range TR1 and the second time range TR2 included in the parent time range TR0 can properly be set. As a result, the first thumbnail image SG1 and the second thumbnail image SG2 suitable for comparison can be generated.

In the second time range setting processing in the time range setting processing (2), processing to set the second time range TR2 so that the second time range TR2 is equal to the overall time range of the parent time range TR0 is performed. That is to say, by setting the second time range TR2 as the parent time range TR0, the first time range TR1 can be set as a part of the second time range TR2 to be focused on. As a result, the first thumbnail image SG1 can be displayed while focusing on the part of the second thumbnail image SG2 to be focused on. A time range with any abnormality can thus be displayed as the first thumbnail image SG1, for example.

In the time range setting processing (3), processing to set the first time range TR1 and the second time range TR2 so that all the time ranges of the first time range TR1 and the second time range TR2 do not overlap each other, and are continuous is further performed. That is to say, since the first time range TR1 and the second time range TR2 are continuous in terms of time, thumbnail images SG can be generated in the continuous time ranges with no omission. As a result, the thumbnail images SG in a continuous time can be displayed in parallel to each other for check in consideration of a time direction. Therefore, in a case where an abnormal part appears and then disappears, for example, diagnosis can be made on a time process thereof.

In the time range setting processing (4), processing to set the first time range TR1 and the second time range TR2 so that the total time range of the first time range TR1 and the second time range TR2 matches the parent time range TR0 is performed. That is to say, throughout the parent time range TR0 as the target for analysis, the thumbnail images SG can be generated in the continuous time ranges with no omission. As a result, the thumbnail images SG in the continuous time throughout the range as the target for analysis can be displayed in parallel to each other for check in consideration of the time direction. Therefore, in a case where the abnormal part appears and then disappears, for example, diagnosis can be made on the time process thereof throughout the range as the target for diagnosis.

In the time range setting processing (5), processing to set the first time range TR1 and the second time range TR2 so that the first time range TR1 and the second time range TR2 include the same number of cardiac periods (dynamic periods) PC is performed. That is to say, since there is no difference in number of cardiac periods PC between time ranges, time ranges suitable for comparison can be set. As a result, the thumbnail images SG can properly be compared with each other independently of the number of cardiac periods PC.

The parent time range setting processing (time range setting unit 120') includes processing to set one of the first time range TR1 and the second time range TR2 as the parent time range TR0$n$ for hierarchical display and processing to newly set the parent time range TR0$n$ for hierarchical display as the parent time range TR0. In the first time range setting processing, processing to newly set the first time range TR1 in the parent time range TR0$n$ for hierarchical display is performed, and, in the second time range setting processing, processing to newly set the second time range TR2 in the parent time range TR0$n$ for hierarchical display is performed. That is to say, by newly setting the first time range TR1 or the second time range TR2 as a new parent time range TR0 (parent time range TR0$n$ for hierarchical display), once-divided time ranges can further be divided into smaller parts. As a result, further-divided thumbnail images SG can be displayed, and thus the thumbnail images SG can specifically be compared with each other for determination.

In the thumbnail generating processing, the statistical value calculating processing to calculate, with respect to the first time range TR1 or the second time range TR2, the pixel statistical value SM (SM1 and SM2) for each corresponding pixel among frame images and the pixel value determining processing to determine the pixel value for the first thumbnail image SG1 or the second thumbnail image SG2 based on the pixel statistical value SM are performed. That is to say, the pixel statistical values SM1 and SM2 in the respective time ranges can be viewed as still images. By generating the thumbnail images SG using the common pixel statistical values SM1 and SM2 (e.g., a maximum value and a total value), the difference in feature between dynamic images in respective time ranges can easily be checked through comparison.

In the statistical value calculating processing, processing to normalize the pixel statistical value SM by the number of cardiac periods PC included in the time range with respect to which the pixel statistical value SM has been calculated is further performed. In a case where the first thumbnail image SG1 and the second thumbnail image SG2 are compared with each other, if each of the pixel statistical values SM1 and SM2 is a total value, the pixel statistical value SM per unit period can be obtained by dividing (normalizing) the total value by the number of cardiac periods PC. That is to say, in a case where the number of cardiac periods PC varies between thumbnail images SG, thumbnail images SG that are equivalent to each other when being compared with each other can be generated. As a result, the thumbnail images SG can properly be compared with each other independently of the number of cardiac periods PC.

Furthermore, since the dynamic period is the cardiac period PC, a cardiac period PC (time period) in which there is any abnormality in blood flow can be specified from the thumbnail images SG, and thus dynamic diagnosis can be made only in the time period in which there is the abnormality. As a result, time required for dynamic diagnosis can be reduced, and dynamic diagnosis can properly and efficiently be made.

<1-5. Modification of Embodiment 1>

As a modification of Embodiment 1, the pixel value determining processing and the thumbnail display method in Embodiment 1 can be changed as follows.

<1-5-1. Thumbnail Generating Processing>

In the pixel value determining processing in the modification of Embodiment 1, colors of pixel values for the thumbnail images SG are set using the pixel statistical values SM1 and SM2 so that the first thumbnail image SG1 and the second thumbnail image SG2 are superimposed onto each other for display. Specifically, if, from among three primary colors <R, G, and B>, the pixel statistical value SM1 is reflected in the R-value, the pixel statistical value SM2 is reflected in the G-value, and the B-value is zero, the first thumbnail image SG1 and the second thumbnail image SG2 can be superimposed onto each other for display as a single thumbnail image SG.

<1-5-2. Thumbnail Display Method (5)>

As a modification of the display unit 34 in Embodiment 1, the display unit 34 may have first and second display modes for displaying the thumbnail images SG (first thumbnail image SG1 and second thumbnail image SG2).

The first display mode herein refers to a mode in which the thumbnail images SG are displayed one by one through switching over time in accordance with a particular rule. The second display mode refers to a mode in which the first thumbnail image SG1 and the second thumbnail image SG2 are superimposed onto each other for display as a single thumbnail image SG using the pixel value set in the above-mentioned pixel value determining processing.

As described above, according to the modification of the image processing apparatus 3 according to Embodiment 1, the display unit 34 has the first and second display modes for displaying the thumbnail images SG, the first display mode is the mode in which the thumbnail images SG are displayed one by one through switching over time in accordance with the particular rule, and the second display mode is the mode in which the first thumbnail image SG1 and the second thumbnail image SG2 are superimposed onto each other for display as a single thumbnail image SG. For example, in a case where the user wants to display desired thumbnail images SG so that the thumbnail images SG can be compared with each other, the thumbnail images SG can easily be compared with each other by displaying the thumbnail images SG one by one through switching or superimposing the thumbnail images SG onto each other for display. As a result, differences can be associated with each other in the two-dimensional space on the thumbnail images SG, and viewed and compared with each other. In addition, an abnormal part is clearly displayed, and thus dynamic diagnosis can properly and efficiently be made.

2. Embodiment 2

A dynamic image for blood flow diagnosis is assumed to be photographed for about 30 seconds, which corresponds to time required for several times of respiration, and thus, if the heart rate is 60 times per minute, 30 periods are photographed in one dynamic image photography. In a case where the overall time TA of the dynamic image is analyzed, if the first thumbnail image SG1 and the second thumbnail image SG2 are generated and displayed for each period, no less than 30 thumbnail images are generated and displayed. Due to the increase in number of thumbnail images SG, a size of each of the thumbnail images SG on a display screen decreases, making it difficult to understand any abnormality of blood flow.

To address the problem, in Embodiment 2, the thumbnail images SG are grouped based on a degree of similarity SI, and hierarchically displayed.

FIG. 23 shows a functional configuration of a control unit 31A of an image processing apparatus 3A in Embodiment 2 of the present invention. The control unit 31A is used as an alternative to the control unit 31 (see FIG. 3) of the image processing apparatus 3 in Embodiment 1. The difference from Embodiment 1 is that a time range setting unit 120A further includes a statistical value calculating unit 124A, a similarity degree calculating unit 125A, and a similarity degree determining unit 126A. The remaining configuration is similar to that of the image processing apparatus 3.

<2-1. Time Range Setting Unit 120A>

The time range setting unit 120A (time range setting processing) includes, in addition to the above-mentioned processing (a1) and (a2), (a3) the statistical value calculating unit 124A (statistical value calculating processing) to calculate, with respect to a plurality of time ranges FTR included in the parent time range TR0, a plurality of pixel statistical values FSM for each corresponding pixel among frame images and (a4) the similarity degree calculating unit 125A (similarity degree calculating processing) to calculate the degree of similarity SI between the time ranges FTR based on the plurality of pixel statistical values FSM calculated with respect to the plurality of time ranges FTR. A first time range setting unit 121A (first time range setting processing) performs processing to set the first time range TR1 in the time ranges FTR based on the degree of similarity SI, and a second time range setting unit 122A (second time range setting processing) performs processing to set the second time range TR2 in the time ranges FTR based on the degree of similarity SI (see FIG. 23). The time ranges FTR can be set in multiples of the cardiac period PC using a plurality of frame images MI' obtained through classification into the cardiac periods PC, for example. The degree of similarity SI corresponds to a difference value between the pixel statistical values FSM calculated with respect to time ranges FTR adjacent to each other in terms of time, and increases as the difference value decreases.

It is herein preferable to dispose the similarity degree determining unit 126A between the similarity degree calculating unit 125A and the first time range setting unit 121A and the second time range setting unit 122A so that the similarity degree determining unit 126A groups the time ranges FTR based on the degree of similarity SI. As a result, the first time range setting unit 121A and the second time range setting unit 122A can respectively set the first time range TR1 and the second time range TR2 based on the grouping.

The statistical value calculating unit 124A has a similar function to the above-mentioned statistical value calculating unit 141. That is to say, the pixel statistical value FSM refers to any of a total value, an average value, a maximum value, a minimum value, a median value, and the like of pixel density calculated with respect to the time ranges FTR using a difference value (pixel density) of a corresponding pixel between frame images MI close to each other in terms of time in the time ranges FTR included in the parent time range TR0. As described above, the pixel statistical value FSM indicates the pixel density, and thus the lack of blood flow and the difference in roughness per cardiac period PC can be determined through comparison.

The similarity degree calculating unit 125A calculates the degree of similarity SI between time ranges FTR adjacent to each other in terms of time in the time ranges FTR based on the pixel statistical values FSM calculated with respect to the time ranges FTR by the statistical value calculating unit 124A, and the similarity degree determining unit 126A groups the time ranges FTR based on the degree of similarity SI. As a method for performing the grouping, the following methods are considered. For example, there is a method of preferentially connecting the time ranges FTR adjacent to each other in terms of time in a case where the degree of similarity SI between the time ranges FTR is high, or preferentially dividing the time ranges FTR adjacent to each other in terms of time in a case where the degree of similarity SI between the time ranges FTR is low. Specifically, there is a method of connecting the time ranges FTR adjacent to each other in terms of time in a case where the degree of similarity SI between the time ranges FTR is higher than a threshold serving as a criterion, or dividing the time ranges FTR adjacent to each other in terms of time in a case where the degree of similarity SI between the time ranges FTR is lower than the threshold. A method of connecting the time ranges FTR adjacent to each other in terms of time until the number of thumbnail images reaches a certain number in a case where the degree of similarity SI between the time ranges FTR is higher than the threshold serving as the criterion, and dividing the time ranges FTR after the number of thumbnail images reaches the certain number is also considered.

In a case as shown in FIG. 14, the threshold serving as the criterion for determining the degree of similarity SI may be different in a case where the first time range TR1 and the second time range TR2 are set in the parent time range TR0 and in a case where the first time range TR1n or the second time range TR2n is set in the parent time range TR0n for hierarchical display.

Figure 24:
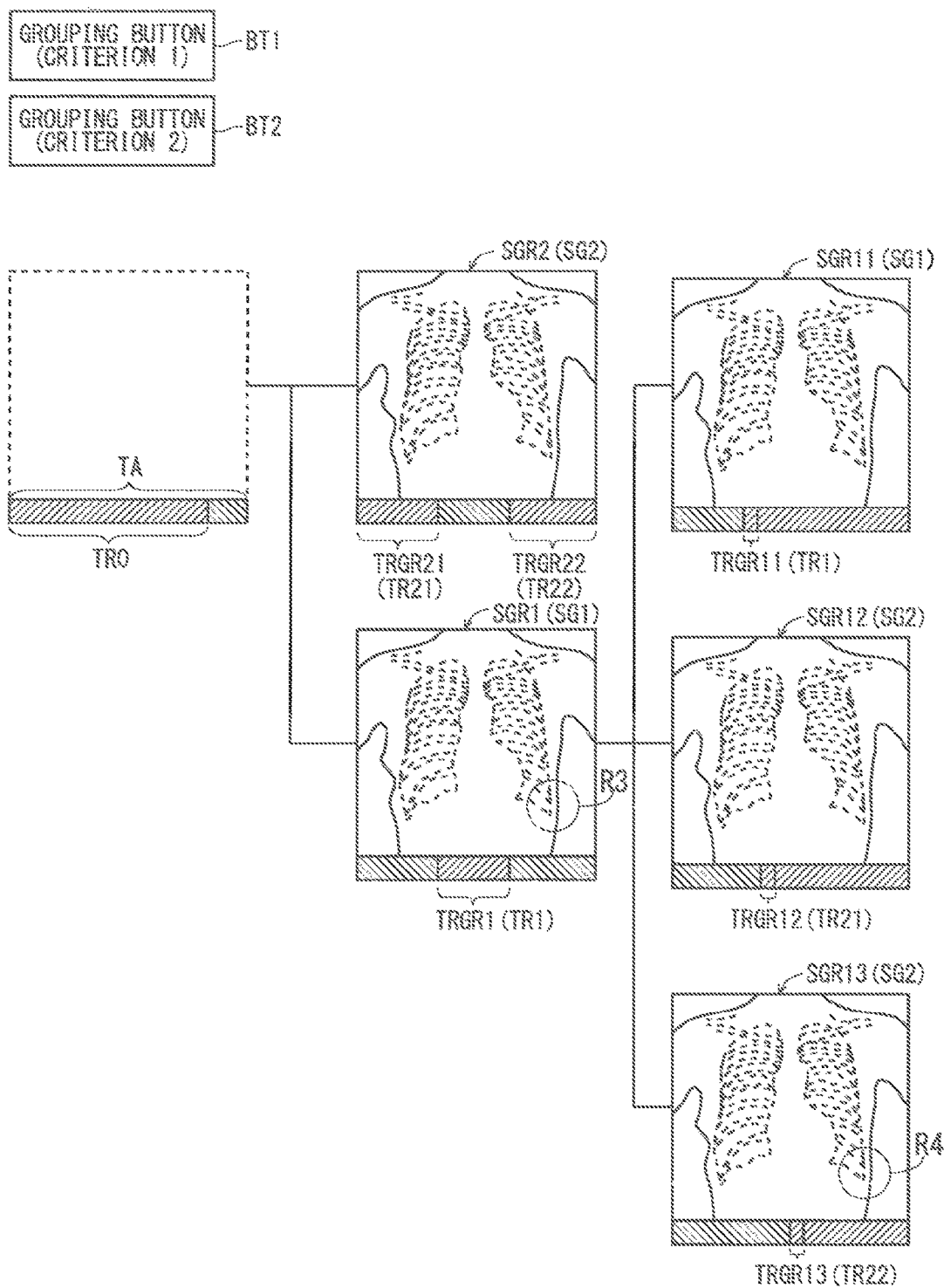
FIG. 24 is a schematic diagram for explaining time range setting processing in Embodiment 2.

FIG. 24 is a diagram for explaining a method for setting the first time range TR1 and the second time range TR2 based on the degree of similarity SI between time ranges FTR included in the parent time range TR0.

As illustrated in FIG. 24, the user designates, as the parent time range TR0, the overall time TA of the dynamic image through the operation unit 33. In this case, the statistical value calculating unit 124A calculates, with respect to the plurality of time ranges FTR included in the parent time range TR0, the plurality of pixel statistical values FSM, and the similarity degree calculating unit 125A calculates the degree of similarity SI between time ranges FTR adjacent to each other in terms of time in the plurality of time ranges FTR based on the plurality of pixel statistical values FSM calculated by the statistical value calculating unit 124A.

When the user presses a grouping button BT1 through the operation unit 33, the similarity degree determining unit 126A groups the time ranges FTR based on the degree of similarity SI. The grouping button BT1 and a grouping button BT2 are different from each other in that the threshold serving as the criterion used when the similarity degree determining unit 126A determines the degree of similarity SI is higher in the case of pressing the grouping button BT2 than in the case of pressing the grouping button BT1. This means that the criterion for determining the degree of similarity SI is stricter in the case of pressing the grouping button BT2 than in the case of pressing the grouping button BT1.

For example, in the parent time range TR0, in a case where the degree of similarity SI between time ranges FTR adjacent to each other in terms of time is equal to or higher than the threshold, the time ranges FTR can be connected to each other to be grouped into a time range TRGR1 (hereinafter, referred to as a "group 1"). Furthermore, if there is any time range, other than the time range TRGR1, that is formed by connecting time ranges FTR adjacent to each other in terms of time in a case where the degree of similarity SI between the time ranges FTR is equal to or higher than the threshold, the time range can be set as a time range (hereinafter, referred to as a "group 2") with a high degree of similarity other than the time range TRGR1. In this case, the first time range setting unit 121A sets the time range TRGR1 as the first time range TR1, and the second time range setting unit 122A sets a time range TRGR2 as the second time range TR2. Alternatively, in a case where the degree of similarity SI between time ranges FTR adjacent to each other in terms of time is lower than the threshold, the time ranges FTR may be grouped into the second time range TR2.

The example of FIG. 24 illustrates a case where a time range that is formed by connecting time ranges FTR adjacent to each other in terms of time in a case where the degree of similarity SI between the time ranges FTR is equal to or higher than the threshold is set as the time range TRGR1, and a time range other than the time range TRGR1, i.e., a time range that is formed by connecting time ranges FTR adjacent to each other in terms of time in a case where the degree of similarity SI between the time ranges FTR is lower than the threshold, is set as the time range TRGR2 (TR21 and TR22).

Therefore, in the example illustrated in FIG. 24, there is no similarity between the time range TRGR1 as the group 1 and the time range TRGR2 as the group 2, the time range TRGR1 is a group of time ranges FTR adjacent to each other in terms of time and meeting the determination criterion that the degree of similarity therebetween is higher than the threshold, and the time range TRGR2 is shown as two time ranges, other than the time range TRGR1, obtained in a case where the degree of similarity between time ranges FTR adjacent to each other is lower than the threshold.

In a case where the user determines that there is a possibility of any abnormality, such as thin blood flow, in a region R3 as a result of viewing a thumbnail image SGR1 (first thumbnail image SG1) in the group 1 determined to have a high degree of similarity SI, the user presses the grouping button BT2 through the operation unit 33 to further divide the time range TRGR1 as the group 1.

As a result, time ranges FTR adjacent to each other in terms of time in the time range TRGR1 are connected or divided based on the determination criterion of the threshold (higher threshold set by the grouping button BT2) for determining the degree of similarity SI, and the time range TRGR1 can consequently be divided into time ranges with a higher degree of similarity.

In the example illustrated in FIG. 24, it can be seen that the time range TRGR1 are divided into three groups, namely, a time range TRGR11, a time range TRGR12, and a time range TRGR13. This means that the time range TRGR1 is further divided into smaller parts with a higher degree of similarity by setting the threshold serving as the criterion for determining the degree of similarity SI for the grouping button BT2 to be higher than the threshold serving as the criterion for determining the degree of similarity SI for the grouping button BT1.

In this case, the first time range setting unit 121A sets the time range TRGR11 as the first time range TR1, and the second time range setting unit 122A sets the time range TRGR12 as the second time range TR21 (TR2) and sets the time range TRGR13 as the second time range TR22 (TR2), for example.

As described above, the first time range setting unit 121A and the second time range setting unit 122A can respectively set the first time range TR1 and the second time range TR2 based on the results of the grouping performed by the similarity degree determining unit 126A with respect to the time range TRGR1 as the group 1.

If the user finds the above-mentioned abnormality, such as thin blood flow, only in a region R4 of a second thumbnail image SG22 as a result of viewing a thumbnail image SGR11 (first thumbnail image SG1) in the time range TRGR11 (first time range TR1), a thumbnail image SGR12 (second thumbnail image SG21) in the time range TRGR12 (second time range TR21), and a thumbnail image SGR13 (second thumbnail SG22) in the time range TRGR13 (second time range TR22), the user can check the dynamic image for the abnormality by narrowing down the time range to the second time range TR22.

In the above-mentioned example of FIG. 24, the user provides an instruction to change the threshold serving as the criterion for determining the degree of similarity SI through the operation unit 33 to perform grouping, but the instruction is not limited to this instruction. For example, an instruction to change the pixel statistical value FSM and an instruction to change a value of a corresponding pixel for obtaining the pixel statistical value FSM may be provided.

In a case where the instruction to change the pixel statistical value FSM is provided, for example, after the degree of similarity SI is obtained using a pixel statistical value FSM that facilitates viewing of the lack to display thumbnail images SG, the degree of similarity SI can further be obtained with respect to a designated thumbnail image SG using a pixel statistical value FSM that facilitates viewing of the delay to display thumbnail images SG. As a result, time determined to have any abnormality can efficiently be analyzed.

For example, the lack can be checked by using a maximum value of the difference value as the pixel statistical value FSM that facilitates viewing of the lack. That is to say, if the maximum value is small, a low pixel density is reflected. Thus, blood flow can be presumed to be poor.

For example, the delay can be checked by using a spatial correlation value of the difference value as the pixel statistical value FSM that facilitates viewing of the delay. That is to say, when the spatial correlation value between a blood flow value (difference value) at a target pixel and blood flow values at pixels spatially surrounding the target pixel is small, the delay in speed of blood flow can be presumed.

In a case where there are a plurality of pixel statistical values FSM, the pixel statistical values FSM may be limited to a single pixel statistical value FSM, or combined to be a single value, for example, through calculation using a norm (distance), a maximum value, a minimum value, an average value, and a median value of the pixel statistical values FSM. Different pixel statistical values FSM may be displayed in different colors so as to be distinguishable. As a result, comparison on the lack of blood flow and the delay can be made simultaneously.

As described above, according to the image processing apparatus 3A in Embodiment 2, the time range setting processing further includes: (a3) the statistical value calculating processing to calculate, with respect to the plurality of time ranges FTR included in the parent time range TR0, the plurality of pixel statistical values FSM for each corresponding pixel among frame images; and (a4) the similarity degree calculating processing to calculate the degree of similarity SI between time ranges FTR adjacent to each other in terms of time in the plurality of time ranges FTR based on the plurality of pixel statistical values FSM calculated with respect to the plurality of time ranges FTR. In the first time range setting processing, processing to set the first time range TR1 in the time ranges FTR based on the degree of similarity SI is performed, and, in the second time range setting processing, processing to set the second time range TR2 in the time ranges FTR based on the degree of similarity SI is performed. For example, the time ranges can be grouped based on the criterion that the degree of similarity SI between time ranges FTR adjacent to each other in terms of time is higher than a predetermined value, and the first time range TR1 and the second time range TR2 can be set based on the grouping. That is to say, by generating a thumbnail image SG in a time range composed of time ranges with a high degree of similarity SI, classification on whether a time range to be specifically analyzed is included can efficiently be performed. In addition, by narrowing down time ranges to the time ranges with the high degree of similarity SI, the number of thumbnail images SG to be visually compared with each other can be reduced.

3. Embodiment 3

FIG. 25 is a diagram showing a functional configuration of a control unit 31B of an image processing apparatus 3B according to Embodiment 3 of the present invention. The control unit 31B is used as an alternative to the control unit 31, (see FIG. 3) of the image processing apparatus 3 in Embodiment 1. The difference from Embodiment 1 is that, since a statistical value calculating unit 141B of a thumbnail generating unit 130B includes a comparison statistical value calculating unit, the pixel value determining unit 142 and the display unit 34 have respectively been changed to a pixel value determining unit 142B and a display unit 34B.

Assumed in the present embodiment is a case where the second time range TR2 includes a plurality of second time ranges TR2, and the second thumbnail image SG2 includes a plurality of second thumbnail images SG2. The remaining configuration is similar to that of the image processing apparatus 3.

<3-1. Thumbnail Generating Unit 130B and Display Unit 34B>

In the thumbnail generating unit 130B, the pixel value determining unit 142B (pixel value determining processing) performs, in addition to the processing performed by the pixel value determining unit 142, processing to determine a pixel value for a first thumbnail image SG1c (hereinafter, referred to as a "thumbnail image SG1c for comparison") or a second thumbnail image SG2c (hereinafter, referred to as a "thumbnail image SG2c for comparison") using a pixel statistical value SMc in a time range TRc for comparison including at least one of the first time range TR1 and the second time range TR2 (see FIG. 25). "Using a pixel statistical value SMc" herein includes using a difference emphasis value DFS based on the pixel statistical value SMc.

Specifically, the statistical value calculating unit 141B performs the following processing in addition to the processing performed by the statistical value calculating unit 141. That is to say, the statistical value calculating unit 141B further performs processing to calculate the pixel statistical value SMc in the time range TRc for comparison and processing to calculate the difference emphasis values DFS based on the pixel statistical values SM1, SM2, and SMc (see FIG. 25).

Assumed herein is a case where the time range TRc for comparison includes three time ranges, namely, (i) the first time range TR1, (ii) the second time range TR2, and (iii) a time range composed of the first time range TR1 and the second time range TR2. For example, in a case where the time range TRc for comparison is (iii), the pixel statistical value SMc may be an average pixel statistical value of the pixel statistical value SM1 in the first time range TR1 and the pixel statistical value SM2 in the second time range TR2, or may be a pixel statistical value obtained by performing the statistical value calculating processing in the time range composed of the first time range TR1 and the second time range TR2.

The difference emphasis values DFS are, for example, values obtained by adding, to the pixel statistical values SM1 and SM2, values based on values obtained by subtracting the respective pixel statistical values SM1 and SM2 from the pixel statistical value SMc.

In the pixel value determining processing performed by the pixel value determining unit 142B, (b1) processing to determine a pixel value for the thumbnail image SG1c for comparison (thumbnail image SG2c for comparison) so that the pixel statistical value SMc and the pixel statistical value SM1 (SM2) are superimposed onto each other for display or (b2) processing to determine a pixel value for the thumbnail image SG1c (SG2c) for comparison based on the difference emphasis value DFS is performed. The thumbnail image SG1c (SG2c) for comparison is therefore generated in the two generating methods (b1) and (b2).

In (b1), the pixel value for the thumbnail image SG1c for comparison (thumbnail image SG2c for comparison) is determined using the pixel statistical value SMc in addition to the pixel statistical value SM1 (SM2). As a specific example of the processing (b1), there is a method of determining the pixel value by, from among three primary colors <R, G, and B>, reflecting the pixel statistical value SM1 (SM2) in the R-value, reflecting the pixel statistical value SMc in the G-value, and setting the B-value as zero, for example. By setting colors of pixels as described above, the pixel statistical value SM1 (SM2) and the pixel statistical value SMc can be superimposed onto each other for display. In (b1) and (b2), the thumbnail image SG1c (SG2c) for comparison is generated separately from the first thumbnail image SG1 (second thumbnail image SG2).

The pixel value determining processing performed by the pixel value determining unit 142B refers to processing to set the pixel value for the thumbnail image based on at least one of (b3) processing to set, with respect to a particular pixel value corresponding to a pixel statistical value SMc or a difference emphasis value DFS that is equal to or higher than a reference value, a color different from a color set with respect to a pixel value corresponding to a pixel statistical value SMc or a difference emphasis value DFS that is equal to or lower than the reference value and (b4) processing to add auxiliary information, such as marking, to the particular pixel value. The reference value may be any value that is determined in advance or designated by the user.

The display unit 34B performs display in response to a command from the pixel value determining unit 142B. In the case of (b1), the thumbnail image SG1c for comparison in which the pixel statistical value SMc and the pixel statistical value SM1 are superimposed onto each other for display (thumbnail image SG2c for comparison in which the pixel statistical value SMc and the pixel statistical value SM2 are superimposed onto each other for display) is displayed. In this case, the first thumbnail image SG1 (second thumbnail image SG2) may be displayed separately, or may not be displayed. In the case of (b2), the thumbnail image SG1c (SG2c) for comparison is displayed separately from the first thumbnail image SG1 (second thumbnail image SG2).

Figure 26:
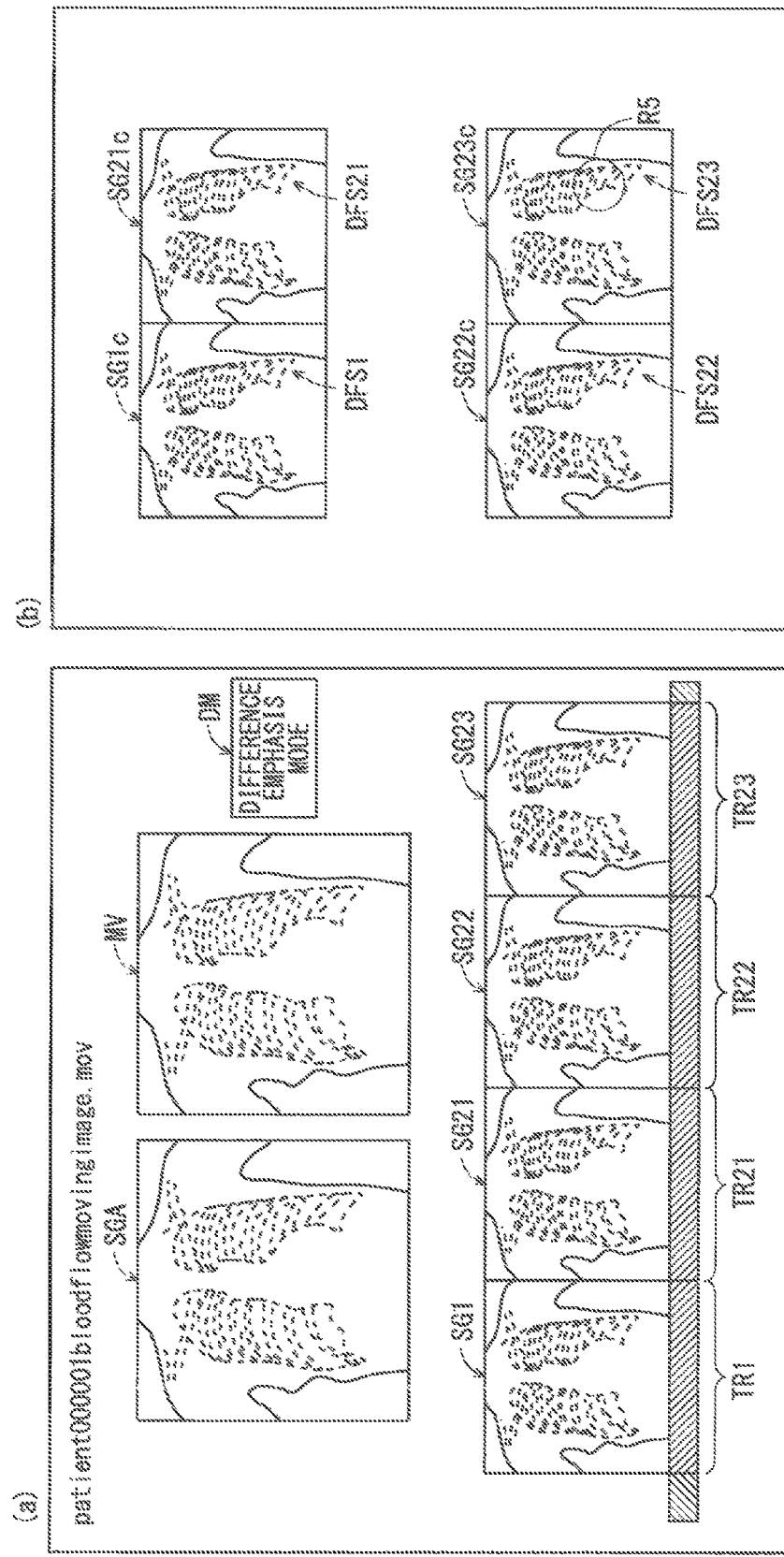
FIG. 26 is a schematic diagram for explaining thumbnail generating processing and a thumbnail display method in Embodiment 3.

FIG. 26 is a schematic diagram for explaining the thumbnail generating processing and the thumbnail display method. Although part (a) of FIG. 264 illustrates a display screen having a similar function to that of part (b) of FIG. 17, the display screen of part (a) of FIG. 26 is different from that of part (b) of FIG. 17 in that it includes a difference emphasis mode DM. Part (b) of FIG. 26 illustrates a display screen displayed when the user presses the difference emphasis mode DM on the display screen of part (a) of FIG. 26 through the operation unit 33.

Part (b) of FIG. 26 illustrates, as an example of the screen, a pop-up screen from the screen illustrated in part (a) of FIG. 26, but the screen is not limited to the pop-up screen. For example, thumbnail images SG1c and SG21c to SG23c for comparison may be displayed in the positions of the first thumbnail image SG1 and the second thumbnail images SG21 to SG23 illustrated in part (a) of FIG. 26 so as to replace the first thumbnail image SG1 and the second thumbnail images SG21 to SG23.

As illustrated in part (a) of FIG. 26, four thumbnail images, namely, the first thumbnail SG1 in the first time range TR1 and the second thumbnail images SG21, SG22, and SG23 in the second time ranges TR21, TR22, and TR23, are generated per cardiac period PC and displayed in parallel to one another. In a case where the user diagnoses an abnormality of blood flow in the second thumbnail image SG23, and then wants to clarify the difference per cardiac period PC, for example, the user presses the difference e emphasis mode DM through the operation unit 33.

Then, the statistical value calculating unit 141B performs processing to calculate the pixel statistical value SMc and the difference emphasis values DFS based on pixel statistical values SM1, SM21, SM22, and SM23 by setting four time ranges, namely, the first time range TR1 and the second time ranges TR21, TR22, and TR23, as the time ranges TRc for comparison. The difference emphasis values DFS in the example of FIG. 26 refer to values obtained by adding, to the pixel statistical values SM (SM1, SM21, SM22, and SM23), values based on values obtained by subtracting the respective pixel statistical values SM from an average pixel statistical value of the pixel statistical values SM (SM1, SM21, SM22, and SM23).

Specifically, the average pixel statistical value, which is represented by Ave, is obtained as "(SM1+SM21+SM22+SM23)/4", and thus difference emphasis values DFS1, DFS21, DFS22, and DFS23 in the first time range TR1 and the second time ranges TR21, TR22, and TR23 can be expressed as follows;

$$DFS1 = SM1 + (SM1 - Ave) \times m \quad (1)$$

$$DFS21 = SM21 + (SM21 - Ave) \times m \quad (2)$$

$$DFS22 = SM22 + (SM22 - Ave) \times m \quad (3)$$

$$DFS23 = SM23 + (SM23 - Ave) \times m \quad (4)$$

Assumed that, in the above-mentioned (1) to (4), calculation is performed at a corresponding pixel among the first thumbnail image SG1 and the second thumbnail images SG21 to SG23. It is preferable that m be a positive coefficient (m>0).

The pixel value determining unit 142B determines the pixel value based on the difference emphasis value DFS through the above-mentioned processing (b2), and the display unit 34B displays the thumbnail images SG1c and SG2c for comparison. That is to say, as illustrated in part (b) of FIG. 26, the "thumbnail image SG1c for comparison" reflecting the difference emphasis value DFS1, the "thumbnail image SG21c for comparison" reflecting the difference emphasis value DFS21, the "thumbnail image SG22c for comparison" reflecting the difference emphasis value DFS22, and the "thumbnail image SG23c for comparison" reflecting the difference emphasis value DFS23 are displayed.

In this case, the pixel value determining unit 142B may set the pixel values for the thumbnail images SG1c and SG2c for comparison by performing the above-mentioned processing (b3) to set, with respect to the particular pixel value corresponding to the difference emphasis value DFS that is equal to or higher than the reference value, the color different from the color set with respect to the pixel value corresponding to the difference emphasis value DFS that is equal to or lower than the reference value, or the above-mentioned processing (b4) to add the auxiliary information to the particular pixel value. A region R5 of the thumbnail image SG23c for comparison illustrated in part (b) of FIG. 26 corresponds to the particular pixel value, and bears a mark as the auxiliary information.

The user checks the abnormality of blood flow in the second thumbnail image SG23 diagnosed beforehand again in the thumbnail images SG1c, SG21c, SG22c, and SG23c for comparison reflecting the difference emphasis values DFS after difference emphasizing. As a result, the user can confirm the abnormality of blood flow in the region R5 of the thumbnail image SG23c for comparison as the abnormality of blood flow is clarified due to difference emphasizing.

FIG. 26 described above illustrates an example in which the time range TRc for comparison is the above-mentioned (iii) time range composed of the first time range TR1 and the second time ranges TR21 to TR23, and the average pixel statistical value of the pixel statistical values SM1 and SM21 to SM23 in the time ranges TR1 and TR21 to TR23 is the pixel statistical value SMc, but the pixel statistical value SMc is not limited to the average pixel statistical value. That is to say, the pixel statistical value SMc may be obtained by performing the statistical value calculating processing in the time range composed of the first time range TR1 and the second time ranges TR21 to TR23.

In part (b) of FIG. 26, the thumbnail images SG1c and SG2c for comparison are generated and displayed through the above-mentioned processing (b2), but the thumbnail images SG1c and SG2c for comparison may be generated and displayed through the above-mentioned processing (b1).

As described above, according to the image processing apparatus 3B in Embodiment 3, the pixel value determining processing further includes processing to determine the pixel value for the first thumbnail image SG1c or the second thumbnail image SG2c (i.e., for the thumbnail image SG1c or SG2c for comparison) using the pixel statistical value SMc in the time range TRc for comparison including at least one of the first time range TR1 and the second time range TR2. That is to say, since the pixel value for the thumbnail image SG1c or SG2c for comparison is determined using the pixel statistical value SMc in the time range TRc for comparison, spatial differences between thumbnail images (in a time direction of the dynamic image) can be associated with each other in the two-dimensional space on the thumbnail images, and viewed and compared with each other. This facilitates understanding of a time-space change of the dynamic image. In addition, the abnormal part can be clarified, and thus dynamic diagnosis can properly and efficiently be made.

In the pixel value determining processing, the difference in pixel value can be clarified through the above-mentioned processing (b3) and (b4), and thus the difference between the thumbnail images SG1c and SG2c for comparison, and eventually the difference in the time direction of the dynamic image can be clarified. As a result, the abnormal part can further be clarified, and thus dynamic diagnosis can more properly and efficiently be made.

4. Modifications

Embodiments of the present invention have been described so far, but the present invention is not limited to the above-mentioned embodiments, and various modifications can be made on the above-mentioned embodiments.

Although the image processing apparatuses 3, 3A, and 3B are described separately in the present embodiments so as to be implemented individually, individual functions of the image processing apparatuses 3, 3A, and 3B may be combined with one another unless any contradiction occurs.

In the image processing apparatus 3 in Embodiment 1, the frame images MI' obtained after classification into the cardiac periods PC output from the period classifying unit 115 are frame images before blood flow analysis (differences between frame images MI) is performed, and blood flow analysis is performed by the statistical value calculating unit 141 of the thumbnail generating unit 130, but the frame images MI' are not limited to this example. The period classifying unit 115 may classify frame images after blood flow analysis is performed into the cardiac periods PC to generate the frame images MI'.

The dynamic period in the present embodiments is described to be the cardiac period PC, but is not limited to the cardiac period PC, and may be a respiratory period. As a result, a respiratory period (time period) with any abnormality can be specified from the thumbnail images SG, and thus dynamic diagnosis can be made only in the time period with the abnormality. Thus, time required for dynamic diagnosis can be reduced, and dynamic diagnosis can properly and efficiently be made.

The subject is not limited to the human body, and may be the body of an animal.

While the present invention has been described in detail, the foregoing description is in all aspects illustrative and not restrictive. It is therefore understood that numerous modifications that have not been described can be devised without departing from the scope of the present invention.

The invention claimed is:

1. An image processing apparatus comprising:
a dynamic image acquiring unit for acquiring a dynamic image including a plurality of frame images obtained by sequentially photographing, in a time direction, a state of a dynamic period in which a physical state in a body of a human or an animal changes periodically;
a time range setting unit for performing time range setting processing including
(a1) first time range setting processing to set, in an overall time of said dynamic image, a first time range composed of one or more dynamic periods, and
(a2) second time range setting processing to set a second time range in the overall time of said dynamic image;
a thumbnail generating unit for performing thumbnail generating processing to generate a first thumbnail image and a second thumbnail image, the first thumbnail image being a still image obtained by performing statistical processing on frame images in said first time range, the second thumbnail image being a still image obtained by performing the statistical processing on frame images in said second time range; and
a display unit for displaying said first thumbnail image and said second thumbnail image so that said first thumbnail image and said second thumbnail image are capable of being visually compared with each other,
wherein said second time range setting processing includes processing to set said second time range composed of one or more dynamic periods.

2. The image processing apparatus according to claim 1, wherein
said time range setting processing includes parent time range setting processing to set, in the overall time of said dynamic image, a parent time range for setting said first time range and said second time range, and
said first time range and said second time range are both included in said parent time range.

3. The image processing apparatus according to claim 2, wherein
said parent time range setting processing includes:
processing to set one of said first time range and said second time range as a parent time range for hierarchical display; and
processing to newly set said parent time range for hierarchical display as said parent time range,
said first time range setting processing includes processing to newly set said first time range in said parent time range for hierarchical display, and
said second time range setting processing includes processing to newly set said second time range in said parent time range for hierarchical display.

4. The image processing apparatus according to claim 2, wherein
said second time range setting processing includes processing to set said second time range so that said second time range is equal to an overall time range of said parent time range.

5. The image processing apparatus according to claim 2, wherein
said time range setting processing further includes processing to set said first time range and said second time range so that all time ranges of said first time range and said second time range do not overlap each other, and are continuous.

6. The image processing apparatus according to claim 5, wherein
said time range setting processing further includes processing to set said first time range and said second time range so that a total time range of said first time range and said second time range matches said parent time range.

7. The image processing apparatus according to claim 2, wherein
said time range setting processing includes processing to set said first time range and said second time range so that all time ranges of said first time range and said second time range include the same number of dynamic periods.

8. The image processing apparatus according to claim 2, wherein
said time range setting processing further includes:
(a3) statistical value calculating processing to calculate, with respect to a plurality of time ranges included in said parent time range, a plurality of pixel statistical values for each corresponding pixel among said frame images; and
(a4) similarity degree calculating processing to calculate a degree of similarity between time ranges adjacent to each other in terms of time in said plurality of time ranges based on said plurality of pixel statistical values calculated with respect to said plurality of time ranges,
said first time range setting processing includes processing to set said first time range in said plurality of time ranges based on said degree of similarity, and
said second time range setting processing includes processing to set said second time range in said plurality of time ranges based on said degree of similarity.

9. The image processing apparatus according to claim 1, wherein
said thumbnail generating processing includes:
statistical value calculating processing to calculate, with respect to said first time range or said second time range, a pixel statistical value for each corresponding pixel among said frame images; and
pixel value determining processing to determine a pixel value for said first thumbnail image or said second thumbnail image based on said pixel statistical value.

10. The image processing apparatus according to claim 9, wherein
said statistical value calculating processing further includes processing to normalize said pixel statistical value by the number of dynamic periods included in said first time range or said second time range with respect to which said pixel statistical value has been calculated.

11. The image processing apparatus according to claim 9, wherein
said pixel value determining processing further includes processing to determine the pixel value for said first thumbnail image or said second thumbnail image using a pixel statistical value in a time range for comparison, the time range for comparison including at least one of said first time range and said second time range.

12. The image processing apparatus according to claim 9, wherein
said pixel statistical value is any of a maximum value, an average value, a minimum value, and a median value of pixel density calculated with respect to said first time range and said second time range for each corresponding pixel among said frame images.

13. The image processing apparatus according to claim 1, further comprising
an operation unit for receiving setting information set by a user, wherein
said setting information includes information for setting a predetermined time range,
said thumbnail generating processing further includes processing to generate a thumbnail image in said predetermined time range indicated by said setting information inputted through said operation unit by performing said statistical processing using frame images in said predetermined time range, and
said display unit performs processing to display the thumbnail image in said predetermined time range.

14. The image processing apparatus according to claim 13, wherein
said setting information further includes information for setting a hidden time range, and
said display unit performs processing to hide said first thumbnail image or said second thumbnail image in a time range included in said hidden time range based on said setting information inputted through said operation unit.

15. The image processing apparatus according to claim 13, wherein
said setting information includes information for setting a predetermined number of time ranges of said first time range and said second time range as an aggregate time range, the predetermined number being two or more,
said thumbnail generating processing further includes processing to generate a thumbnail image in said aggregate time range indicated by said setting information inputted through said operation unit by performing said statistical processing using frame images in said aggregate time range, and
said display unit performs:
processing to hide a predetermined number of thumbnail images in time ranges included in said aggregate time range; and
processing to display the thumbnail image in said aggregate time range.

16. The image processing apparatus according to claim 1, further comprising
an operation unit for receiving setting information set by a user, wherein
said setting information includes information for setting one of said first thumbnail image and said second thumbnail image as a thumbnail image for moving image comparison, and
said display unit performs processing to play back a dynamic image corresponding to said thumbnail image for moving image comparison based on said setting information inputted through said operation unit.

17. The image processing apparatus according to claim 1, wherein
said dynamic period includes a cardiac period or a respiratory period.

18. A computer-readable non-transitory storage medium storing a program executed by a computer included in an image processing apparatus according to claim 1.

19. An image processing apparatus comprising:
a dynamic image acquiring unit for acquiring a dynamic image including a plurality of frame images obtained by sequentially photographing, in a time direction, a state of a dynamic period in which a physical state in a body of a human or an animal changes periodically;
a time range setting unit for performing time range setting processing including
(a1) first time range setting processing to set, in an overall time of said dynamic image, a first time range composed of one or more dynamic periods, and
(a2) second time range setting processing to set a second time range in the overall time of said dynamic image;
a thumbnail generating unit for performing thumbnail generating processing to generate a first thumbnail image and a second thumbnail image, the first thumbnail image being a still image obtained by performing statistical processing on frame images in said first time range, the second thumbnail image being a still image obtained by performing the statistical processing on frame images in said second time range; and
a display unit for displaying said first thumbnail image and said second thumbnail image so that said first thumbnail image and said second thumbnail image are capable of being visually compared with each other,
wherein said time range setting processing includes parent time range setting processing to set, in the overall time of said dynamic image, a parent time range for setting said first time range and said second time range, and
said first time range and said second time range are both included in said parent time range.

20. An image processing apparatus comprising:
a dynamic image acquiring unit for acquiring a dynamic image including a plurality of frame images obtained by sequentially photographing, in a time direction, a state of a dynamic period in which a physical state in a body of a human or an animal changes periodically;
a time range setting unit for performing time range setting processing including
(a1) first time range setting processing to set, in an overall time of said dynamic image, a first time range composed of one or more dynamic periods, and
(a2) second time range setting processing to set a second time range in the overall time of said dynamic image;
a thumbnail generating unit for performing thumbnail generating processing to generate a first thumbnail image and a second thumbnail image, the first thumbnail image being a still image obtained by performing statistical processing on frame images in said first time range, the second thumbnail image being a still image obtained by performing the statistical processing on frame images in said second time range; and
a display unit for displaying said first thumbnail image and said second thumbnail image so that said first thumbnail image and said second thumbnail image are capable of being visually compared with each other,
wherein said thumbnail generating processing includes:
statistical value calculating processing to calculate, with respect to said first time range or said second time range, a pixel statistical value for each corresponding pixel among said frame images; and
pixel value determining processing to determine a pixel value for said first thumbnail image or said second thumbnail image based on said pixel statistical value.

* * * * *